United States Patent
Vuillemin et al.

(10) Patent No.: US 10,308,724 B2
(45) Date of Patent: Jun. 4, 2019

(54) VERY HIGH MOLAR MASS DEXTRANS

(71) Applicants: INSTITUT NATIONAL DES SCIENCES APPLIQUÉES DE TOULOUSE, Toulouse (FR); INSTITUT NATIONAL DE LA RECHERCHE AGRONOMIQUE, Paris (FR); CENTRE NATIONAL DE LA RECHERCHE SCIENTIFIQUE, Paris (FR); UNIVERSITE DE BORDEAUX, Bordeaux (FR); INSTITUT POLYTECHNIQUE DE BORDEAUX, Pessac (FR)

(72) Inventors: Marlène Vuillemin, Ramonville-Saint-Agne (FR); Marion Claverie, Benejacq (FR); Claire Moulis, Viellevigne (FR); Magali Remaud-Simeon, Ramonville-Saint-Agne (FR); Florent Grimaud, Castanet-Tolosan (FR); Pierre Monsan, Mondonville (FR); Agnès Sabate, Treillieres (FR); Catherine Garnier, Nantes (FR); Marguerite Dols-Lafargue, Fargues-Saint-Hilaire (FR); Patrick Lucas, Martillac (FR)

(73) Assignees: INSTITUT NATIONAL DES SCIENCES APPLIQUEES TOULOUSE, Toulouse (FR); INSTITUT NATIONAL DE LA RECHERCHE AGRONOMIQUE, Paris (FR); CENTRE NATIONAL DE LA RECHERCHE SCIENTIFIQUE, Paris (FR); UNIVERSITE DE BORDEAUX, Bordeaux (FR); INSTITUT POLYTECHNIQUE DE BORDEAUX, Pessac (FR)

(*) Notice: Subject to any disclaimer, the term of this patent is extended or adjusted under 35 U.S.C. 154(b) by 0 days.

(21) Appl. No.: 15/319,736

(22) PCT Filed: Jun. 19, 2015

(86) PCT No.: PCT/EP2015/063864
§ 371 (c)(1),
(2) Date: Dec. 16, 2016

(87) PCT Pub. No.: WO2015/193492
PCT Pub. Date: Dec. 23, 2015

(65) Prior Publication Data
US 2017/0145120 A1 May 25, 2017

(30) Foreign Application Priority Data

Jun. 20, 2014 (FR) .................... 14 55751

(51) Int. Cl.
| | |
|---|---|
| C12P 19/08 | (2006.01) |
| C08B 37/02 | (2006.01) |
| C12P 19/18 | (2006.01) |
| C12N 9/10 | (2006.01) |
| C08B 37/00 | (2006.01) |
| C08L 5/02 | (2006.01) |
| A61K 8/73 | (2006.01) |
| A23L 29/269 | (2016.01) |
| A61Q 19/00 | (2006.01) |

(52) U.S. Cl.
CPC ........ *C08B 37/0021* (2013.01); *A23L 29/273* (2016.08); *A61K 8/73* (2013.01); *A61Q 19/00* (2013.01); *C08B 37/0009* (2013.01); *C08L 5/02* (2013.01); *C12N 9/1051* (2013.01); *C12P 19/08* (2013.01); *C12P 19/18* (2013.01); *C12Y 204/01005* (2013.01); *A23V 2002/00* (2013.01); *A61K 2800/10* (2013.01); *A61K 2800/48* (2013.01)

(58) Field of Classification Search
None
See application file for complete search history.

(56) References Cited

FOREIGN PATENT DOCUMENTS

| | | |
|---|---|---|
| WO | 03/008618 A2 | 1/2003 |
| WO | 2013/017330 A1 | 2/2013 |

OTHER PUBLICATIONS

H.H. Guo et al. "Protein tolerance to random amino acid change", PNAS 101(25):9205-9210 (Year: 2004).*
Genbank Accession No. G9WG05—http://www.uniprot.org/uniprot/G9WG05.txt?version=15, retrieved May 2, 2015, 2 pages.
Ahmed et al., "Characterization of high molecular weight dextran produced by *Weissella cibaria* CMGDEX3," *Carbohydrate Polymers* 90:441-446, 2012.
Endo et al., "*Oenococcus kitaharae* sp. nov., a non-acidophilic and non-malolactic-fermenting oenococcus isolated from a composting distilled shochu residue," *International Journal of Systematic and Evolutionary Microbiology* 56:2345-2348, 2006.
Rühmkorf et al., "Effect of structurally different microbial homoexopolysaccharides on the quality of gluten-free bread," *Eur Food Res Technol* 235:139-146, 2012.
André et al., "Sucrose-Utilizing Transglucosidases for Biocatalysis," *Top Curr. Chem.* 294:25-48, 2010.
Leemhuis et al., "Glucansucrases: Three-dimensional structures, reactions, mechanism, α-glucan analysis and their implications in biotechnology and food applications," *Jl. of Biotechnology* 163:250-272, 2013.

(Continued)

*Primary Examiner* — Rebecca E Prouty
(74) *Attorney, Agent, or Firm* — Seed Intellectual Property Law Group LLP

(57) ABSTRACT

The subject matter of the invention is dextrans which have between 95% and 99% of α-1,6 glucosidic bonds, a weight-average molar mass $M_w$ at least equal to $0.7 \times 10^9$ g.mol$^{-1}$, and a dispersity index D of between 1.3 and 3. The invention also relates to a dextran saccharase which makes it possible to produce such dextrans, and to a method for producing said dextrans.

6 Claims, 15 Drawing Sheets

Figure 1:
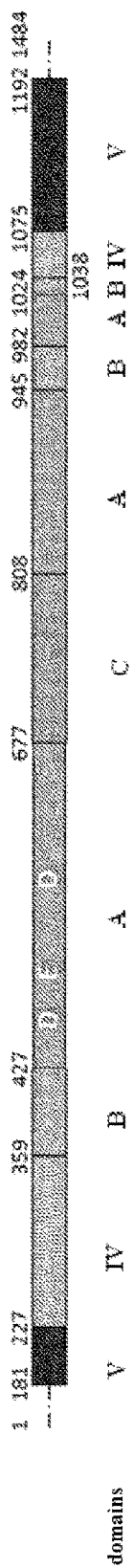

Specification includes a Sequence Listing.

(56) References Cited

OTHER PUBLICATIONS

Monchois et al., "Glucansucrases: mechanism of action and structure-function relationships," *FEMS Microbiology Reviews* 23:131-151, 1999.
Monsan et al., "Transglucosidases as efficient tools for oligosaccharide and glucoconjugate synthesis," *Current Opinion in Microbiology* 13:293-300, 2010.
Moulis et al., "One-step synthesis of isomalto-oligosaccharide syrups and dextrans of controlled size using engineered dextransucrase," *Biocatalysis and Biotransformation* 26(1-2):141-151, 2008.
van Hijum et al., "Structure-Function Relationships of Glucansucrase and Fructansucrase Enzymes from Lactic Acid Bacteria," *Microbiology and Molecular Biology Reviews* 70(1):157-176, 2006.
Uitdehaag et al., "Catalytic mechanism and product specificity of cyclodextrin glycosyltransferase, a prototypical transglycosylase from the α-amylase family," *Enzyme and Microbial Technology* 30:295-304, 2002.

\* cited by examiner

SEQUENCE LISTING

<160> NUMBER OF SEQ ID NOS: 3

<210> SEQ ID NO 1
<211> LENGTH: 1484
<212> TYPE: PRT
<213> ORGANISM: Artificial Sequence
<220> FEATURE:
<223> OTHER INFORMATION: Oenococcus kitaharae

<400> SEQUENCE: 1

```
Met Met Ala Thr Gly Ser Asn Leu Ile Thr Ala Gln Ala Asp Asp Leu
1               5                   10                  15

Asn Gln Glu Gly Thr Ala Ala Gln Ser Val Ser Pro Ser Thr Ala Ala
                20                  25                  30

Ala Asn Gln Ser Glu Ser Ser Ala Gln Ser Thr Glu Gln Ser Ala Thr
            35                  40                  45

Gln Ala Ala Thr Asp Gly Glu Ala Ser Thr Val Ser Thr Ala Val Thr
        50                  55                  60

Thr Ile Thr Pro His Tyr Val Gln Ala Gly Lys Trp Leu Tyr Met
65                  70                  75                  80

Gly Ser Asp Gly Glu Phe Val Lys Gly Pro Gln Thr Ile Asp Gly Asn
                85                  90                  95

Leu Gln Phe Phe Asp Glu Gln Gly Ile Gln Ile Lys Gly Ser Phe Glu
            100                 105                 110

Thr Val Asp Gly Ser Ser Tyr Tyr Phe Asp Ser Gln Ser Gly Asn Ala
        115                 120                 125

Val Thr Gly Phe Lys Ile Ile Asn Asn Asp Leu His Tyr Phe Glu Glu
    130                 135                 140

Asp Gly Lys Glu Thr Val Asn Asn Tyr Ala Thr Asp Lys Gln Gly Asn
145                 150                 155                 160

Ile Phe Tyr Phe Asp Glu Asn Gly Gln Met Ala Thr Gly Val Lys Thr
                165                 170                 175

Ile Gln Gly Gln Ser Tyr Tyr Phe Asp Gln Asp Gly His Met Arg Lys
            180                 185                 190

Gly Tyr Ser Gly Val Phe Asp Asn Gln Val Leu Tyr Phe Asp Lys Thr
        195                 200                 205

Thr Gly Ala Leu Ala Asn Thr Asn Val Ser Ser Ile Lys Glu Gly Leu
    210                 215                 220

Thr Ala Gln Asn Asp Asp Phe Thr Ala His Asn Ala Val Tyr Ser Thr
225                 230                 235                 240

Lys Ser Glu Ser Phe Thr Asn Ile Asp Gly Tyr Leu Thr Ala Glu Ala
                245                 250                 255

Trp Tyr Arg Pro Ala Asp Ile Leu Glu Asn Gly Thr Asp Trp Arg Ala
            260                 265                 270

Ser Arg Ala Asp Glu Phe Arg Pro Ile Leu Thr Thr Trp Trp Pro Asp
        275                 280                 285

Lys Gln Thr Glu Val Asn Tyr Leu Asn Tyr Met Lys Thr Gln Gly Phe
    290                 295                 300

Ile Thr Asn Asp Gln Asp Phe Lys Leu Ser Asp Gln Leu Leu Leu
305                 310                 315                 320

Asn His Ala Ala Gln Ser Val Gln Gly Glu Ile Glu Lys Lys Ile Ser
                325                 330                 335

Gln Gln Gly Ser Thr Asp Trp Leu Lys Thr Leu Leu Gly Thr Phe Ile
            340                 345                 350

Asn Gln Gln Pro Ser Trp Asn Gly Glu Ser Glu Asp Pro Gly Ser Asp
```

-continued

```
                355                 360                 365
His Leu Gln Gly Gly Ala Leu Thr Phe Val Asn Ser Pro Leu Thr Pro
    370                 375                 380
Asp Ser Asn Ser Asn Phe Arg Leu Leu Asn Arg Thr Pro Thr Asn Gln
385                 390                 395                 400
Thr Gly Thr Pro Gln Tyr Asp Thr Asp Ala Ser Leu Gly Gly Phe Glu
                405                 410                 415
Leu Leu Leu Ala Asn Asp Val Asp Asn Ser Asn Pro Val Val Gln Ala
                420                 425                 430
Glu Gln Leu Asn Trp Leu Tyr Tyr Leu Leu Asn Phe Gly Ser Ile Thr
                435                 440                 445
Ala Asp Asp Pro Asn Ala Asn Phe Asp Gly Ile Arg Ile Asp Ala Val
                450                 455                 460
Asp Asn Val Asp Ala Asp Leu Leu Gln Ile Ala Ala Tyr Phe Lys
465                 470                 475                 480
Asp Ala Phe Lys Ser Gly Ser Asn Asp Gln Thr Thr Asn Gln His Leu
                485                 490                 495
Ser Ile Leu Glu Asp Trp Ser His Asn Asp Pro Glu Tyr Met Lys Ala
                500                 505                 510
Gln Gly Tyr Pro Gln Leu Thr Met Asp Asp Tyr Met His Thr Gln Leu
                515                 520                 525
Ile Trp Ser Leu Thr Lys Pro Asp Asn Ile Arg Gly Thr Met Gln Arg
                530                 535                 540
Phe Met Asp Tyr Tyr Leu Val Asn Arg Ala Asn Asp Ser Thr Asn Asn
545                 550                 555                 560
Glu Ala Val Ala Asn Tyr Ser Phe Val Arg Ala His Asp Ser Glu Val
                565                 570                 575
Gln Thr Val Ile Ala Gln Ile Ile Ser Asp Leu Tyr Pro Asn Ser Gly
                580                 585                 590
Ser Gly Leu Ile Pro Thr Thr Asp Gln Leu Gln Ala Ala Phe Glu Val
                595                 600                 605
Tyr Asn Ala Asp Met Lys Ser Asp Val Lys Lys Tyr Thr Gln Tyr Asn
                610                 615                 620
Ile Pro Ser Ala Tyr Ala Met Leu Leu Thr Asn Lys Asp Thr Val Pro
625                 630                 635                 640
Arg Val Tyr Tyr Gly Asp Met Tyr Thr Asp Gly Asp Tyr Met Ala
                645                 650                 655
Asn Lys Ser Pro Tyr Phe Asp Ala Ile Ser Thr Leu Leu Lys Ala Arg
                660                 665                 670
Val Lys Tyr Ala Ala Gly Gly Gln Ser Met Ala Val Asp Lys Asn Asp
                675                 680                 685
Ile Leu Thr Ser Val Arg Phe Gly Gln Asn Ala Met Leu Ala Ser Asp
                690                 695                 700
Ser Gly Asp Asn Gln Thr Arg Gln Glu Gly Ile Gly Val Ile Val Ser
705                 710                 715                 720
Asn Asn Ser His Leu Lys Leu Ala Glu Asn Asp Gln Val Val Leu His
                725                 730                 735
Met Gly Ala Ala His Lys Asn Gln Ala Phe Arg Ala Leu Leu Leu Thr
                740                 745                 750
Ile Glu Ser Gly Leu Glu Asn Phe Asp Thr Asp Leu Gln Ala Pro Val
                755                 760                 765
Lys Tyr Thr Asp Ala Asn Gly Asp Leu Ile Phe Thr Ala Ala Glu Leu
                770                 775                 780
```

```
Ala Gly Tyr Leu Asn Pro Glu Val Ser Gly Tyr Leu Ser Ala Trp Val
785                 790                 795                 800

Pro Val Gly Ala Ala Asp Asn Gln Asp Ala Arg Thr Ala Ala Asp Ser
            805                 810                 815

Ala Thr Ser Thr Asp Gly Asn Val Phe His Ser Asn Ala Ala Leu Asp
        820                 825                 830

Ser Asn Val Ile Phe Glu Gly Phe Ser Asn Phe Gln Ser Ile Pro Thr
            835                 840                 845

Ala Glu Gln His Asp Asp Phe Thr Asn Val Lys Ile Ala Glu Asn Ala
850                 855                 860

Gly Leu Phe Lys Asp Trp Gly Ile Thr Ser Phe Gln Leu Ala Pro Gln
865                 870                 875                 880

Tyr Arg Ser Ser Thr Asp Ser Thr Phe Leu Asp Ser Ile Ile Gln Asn
                885                 890                 895

Gly Tyr Ala Phe Thr Asp Arg Tyr Asp Leu Gly Phe Asp Thr Pro Thr
            900                 905                 910

Lys Tyr Gly Asp Val Asp Asp Leu Arg Ala Ala Ile Lys Ala Leu His
        915                 920                 925

Ala Asn Asn Ile Gln Val Met Ala Asp Trp Val Pro Asp Gln Ile Tyr
930                 935                 940

Asn Leu Gln Asn Pro Glu Ile Ile Thr Val Asn Arg Thr Asp Ser Tyr
945                 950                 955                 960

Gly Gln Pro Ile Ala Gly Ser Asp Leu Gln Asn Asp Leu Tyr Leu Ala
                965                 970                 975

Tyr Thr Asn Gly Gly Gln Tyr Gln Thr Lys Phe Gly Gly Ala Phe
            980                 985                 990

Leu Glu Lys Leu Gln Gln Leu Tyr Pro Asp Leu Phe Thr Lys Thr Gln
        995                 1000                1005

Ile Ser Thr Gly Gln Thr Ile Asp Pro Ser Gln Lys Ile Thr Glu
    1010                1015                1020

Trp Ser Ala Lys Tyr Phe Asn Gly Ser Asn Ile Gln Gly Arg Gly
    1025                1030                1035

Ala Tyr Tyr Val Leu Arg Asp Ser Gly Thr Asp Gln Tyr Phe Lys
    1040                1045                1050

Val Ile Ser Asn Asp Glu Asn Glu Ala Phe Leu Pro Lys Gln Leu
    1055                1060                1065

Thr Asn Gln Pro Gly Glu Thr Gly Phe Ser Gln Asp Gln Gly
    1070                1075                1080

Ile Ile Phe Phe Ser Thr Ser Gly Tyr Gln Ala Lys Asn Ala Phe
    1085                1090                1095

Val Gln Gly Asp Asp Gly Asn Tyr Tyr Tyr Phe Asp Asn Thr Gly
    1100                1105                1110

His Met Val Thr Gly Pro Gln Thr Ile Asn Gly Arg His Tyr Leu
    1115                1120                1125

Phe Phe Pro Asn Gly Val Glu Ala Gln Asn Val Phe Val Gln Asn
    1130                1135                1140

Asp Arg Gly Glu Thr Tyr Tyr Asp Gln Arg Gly Arg Gln Val
    1145                1150                1155

Ala Asn Gln Tyr Val Thr Asp Thr Asn Gly Asn Ser Phe Arg Phe
    1160                1165                1170

Asp Glu Asn Gly Ile Met Leu Ala Asn Gln Leu Ala Gln Val Asp
    1175                1180                1185
```

Gly His Trp Gln Phe Phe Lys Ser Ser Gly Val Gln Ala Lys Asp
    1190                1195                1200

Ala Phe Ile Leu Gly Ser Asp Gly Lys Leu Arg Tyr Phe Glu Ser
    1205                1210                1215

Gly Asn Gly Asn Met Ala Val Asn Glu Phe Lys Gly Ser Glu Asn
    1220                1225                1230

Gly Arg Tyr Tyr Tyr Phe Gly Ala Asp Gly Gln Ala Val Ser Gly
    1235                1240                1245

Leu Gln Thr Ile Asn Gly Arg Gln Leu Tyr Phe Asp Asp His Gly
    1250                1255                1260

Gln Gln Met Lys Asp Ala Phe Tyr Thr Asn Gln Ser Gly Gln Arg
    1265                1270                1275

Phe Tyr Phe Asn Ala Leu Thr Gly Asp Leu Val Lys Gly Asn Phe
    1280                1285                1290

Ile Tyr Thr Ser Ala Ser Ser Phe Thr Pro Asp Asn Asp Ser
    1295                1300                1305

Ser Asp Ser Tyr Gln Gly Asp Ser His Leu Trp Tyr Tyr Ala Asp
    1310                1315                1320

Ser Gln Gly Gln Ile Val Thr Gly Phe Gln Thr Ile Asn Gly His
    1325                1330                1335

Leu Gln Tyr Phe Asp Asp Ile Ser Gly Gln Met Ile Thr Asn Arg
    1340                1345                1350

Phe Met Arg Arg Ala Asp Gly Asn Trp Ile Tyr Leu Asp Glu Asn
    1355                1360                1365

Gly Glu Ala Val Arg Gly Met Arg Val Ile Asn Gly Leu Thr Asn
    1370                1375                1380

Tyr Phe Arg Asp Asp Phe Thr Gln Val Lys Asp Gly Phe Ala Gln
    1385                1390                1395

Asp Pro Asn Ser Gly Glu Arg His Tyr Phe Asn Gly Thr Asn Gly
    1400                1405                1410

Ala Met Val Thr Asn Asp Tyr Phe Ser Pro Asp Gln Ile His Trp
    1415                1420                1425

Tyr Tyr Ala Asp Asp Ser Gly Gln Pro Val Thr Gly Phe Gln Thr
    1430                1435                1440

Ile Lys Gly Gln Val Gln Tyr Phe Asp Gln Asp Gly Ile Gln Leu
    1445                1450                1455

Lys Gly Gly Ser Gln Thr Asp Pro Val Thr Lys Gln Thr Tyr Tyr
    1460                1465                1470

Phe Asp Asp Lys Phe Gly Asn Gly Gln Ile Leu
    1475                1480

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
caccatgatg gcgaccggct c                                         21

<210> SEQ ID NO 3
<211> LENGTH: 28
<212> TYPE: DNA
<213> ORGANISM: Artificial Sequence
<220> FEATURE:
<223> OTHER INFORMATION: primer

```
<400> SEQUENCE: 3
gaggatttga ccgtttccaa acttatcg                                          28
```

VERY HIGH MOLAR MASS DEXTRANS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480373_401USPC_SEQUENCE_LISTING.txt. The text file is 13.5 KB, was created on Dec. 14, 2016, and is being submitted electronically via EFS-Web.

The invention relates to very high molar mass dextrans which at the same time have a low dispersity index.

Unless otherwise indicated, the term "molar mass" or "average molar masses" is intended to mean, in the present invention, the weight-average molar mass.

The invention also relates to a dextransucrase which makes it possible to produce such dextrans, and to a process for producing said dextrans.

Glucansucrases of bacterial origin are transglucosylases belonging to glycoside hydrolase families 13 and 70. These enzymes catalyze, from sucrose, the synthesis of α-glucans formed from glucosyl units. They can also synthesize oligosaccharides or glucoconjugates by transglucosylation reaction on exogenous acceptors of varied natures. Glucansucrases exhibit different product specificities, both in terms of the glycosidic bonds synthesized (α-1,2; α-1,3; α-1,4 or α-1,6) and in terms of the organization of these bonds within the products formed.

Generally, glucansucrases are naturally produced by lactic acid bacteria, for example of the genera *Leuconostoc, Lactobacillus, Streptococcus* or *Weissela* sp.

Among glucansucrases, dextransucrases produce dextran, generally having at least 50% of α-1,6 glycosidic bonds in the main chain, and α-1,2, α-1,3 and/or α-1,4 branches. The amount of branches and also the spatial arrangement thereof vary according to the producing enzyme.

Dextrans and dextran derivatives have an increasing number of industrial applications, which depend on their sizes. Dextrans of low or medium molar mass (generally ranging from $10^3$ to $7\times10^4$ g.mol$^{-1}$) are in particular used for analytical applications, for example as versatile supports for chromatography, in the medical field, for example as a blood plasma expander by virtue of their weak antigenic nature and their low viscosity in saline solution, as an iron transporter or anticoagulant (after functionalization), in the prevention of post-operative shock, in the treatment of burns or in the reduction of the risks of thrombosis or of embolisms.

The *Leuconostoc mesenteroides* NRRL B-512F strain is one of the microorganisms that has been the most widely used for many years for the industrial production of dextrans. This strain makes it possible to obtain dextrans of very high molar mass, ranging from $10^6$ to more than $10^8$ g.mol$^{-1}$. The enzyme responsible for this synthesis is the dextransucrase called DSR-S. This glucose homopolymer has 95% of α-1,6 glucosidic bonds and 5% of α-1,3 glucosidic bonds (1). However, the dextrans produced by *Leuconostoc mesenteroides* NRRL B-512F are highly polydisperse and have a rheological behavior, and in particular a viscosifying capacity, limiting their use as a texturing agent.

It has been possible to clone, in *Escherichia coli*, the gene encoding DSR-S (1,2), enabling the construction of various DSR-S variants. In particular, forms truncated in the N- and C-terminal domains of DSR-S synthesize, directly from sucrose, dextrans of controlled molar masses of $4.1\times10^8$, $40\times10^3$ or $1\times10^3$ g.mol$^{-1}$. One of them, called DSR-S vardel Δ4N and produced in recombinant form by *Escherichia coli*, catalyzes, from sucrose, the synthesis of a dextran with a molecular mass evaluated at $4.1\times10^8$ g.mol$^{-1}$ and consisting of 96% of α-1,6 bonds and 4% of α-1,3 bonds. The dextran solution obtained with DSR-S vardel Δ4N has a viscosity that is greater by a factor of 10 to 100, depending on the shear stress applied, compared with that obtained with the DSR-S enzyme, and exhibits a shear-thinning behavior. The dextran obtained with DSR-S vardel Δ4N thus proves to be particularly advantageous for applications in the texturing agent field. However, the viscosity of this polymer greatly decreases when constant shear stresses of long duration are applied.

The dextrans produced by the glucansucrases known up to now thus have drawbacks, in particular associated with high dispersity indices or with medium molar masses which do not exceed approximately $10^8$ g.mol$^{-1}$, and also relatively limited rheological properties, in particular a relatively limited texturing capacity.

There is thus still a need for novel dextrans of which the properties make it possible to broaden the field of applications of polymers of this type.

The inventors have thus, to their credit, produced dextrans which have an extremely high molar mass, much higher than was produced up until now, while at the same time having a low dispersity index. These characteristics in particular confer on them physicochemical properties that are particularly original in comparison with the dextrans synthesized up until now.

The dextrans in accordance with the invention are characterized in that they have between 95% and 99%, preferably between 97% and 98%, more preferably between 97.4% and 97.6%, of α-1,6 glucosidic bonds, a weight-average molar mass $M_w$ at least equal to $0.7\times10^9$ g.mol$^{-1}$, and a dispersity index $D_i$ of between 1.3 and 3.

Typically, to determine the weight-average molar mass, the method described in the examples may be used.

According to one particular embodiment of the invention, the dextrans in accordance with the invention have a weight-average molar mass $M_w$ at least equal to $1\times10^9$ g.mol$^{-1}$. Typically, the weight-average molar mass $M_w$ of the dextrans in accordance with the invention is less than $5\times10^{10}$, preferably less than $1\times10^{10}$, preferably less than $5\times10^9$ g.mol$^{-1}$.

The dextrans in accordance with the invention thus have the advantage of having an extremely high and controlled molar mass, of the order of 10 times higher than the dextrans synthesized up until now.

In addition, the dextrans in accordance with the invention have a dispersity index $D_i$ of between 1.3 and 3, preferably of between 1.5 and 2.5. More preferably, the dispersity index $D_i$ is 1.8±0.3. Thus, although their molar mass is very high, the dextrans in accordance with the invention also have the advantage of having a low dispersity index. In comparison, a commercial dextran of $2\times10^6$ Da has a dispersity index of 3.49 (11).

A "virtually linear" polymer or dextran is the term used herein to refer to a polymer or a dextran of which the degree of branching is low and/or the hydrodynamic coefficient $\upsilon_G$ is between 0.44 and 0.52, preferably between 0.46 and 0.50, preferably 0.48. Thus, the dextrans in accordance with the invention have between 95% and 99%, preferably between 97% and 98%, more preferably between 97.4% and 97.6%, of α-1,6 glucosidic bonds. The dextrans in accordance with the invention also advantageously have between 1% and 5%, preferably between 2% and 3%, more preferably between 2% and 2.5%, of α-1,3 glucosidic bonds. Particularly advantageously, the dextrans in accordance with the invention have 97.55% of α-1,6 glucosidic bonds and 2.45% of α-1,3 glucosidic bonds. The dextrans in accordance with the invention are thus virtually linear.

The particular structural characteristics of the dextrans according to the invention confer thereon particularly advantageous physicochemical properties, allowing their use in many applications, and in particular in the oil industry or the cosmetics industry or in food processing.

With regard to the rheological properties, the dextrans in accordance with the invention have a high dynamic viscosity for low shear rates and exhibit a shear-thinning or pseudoplastic behavior, their dynamic viscosity decreasing with an increase in the rate gradient (or shear rate), as described in example 12.

Moreover, the viscosity of the dextrans in accordance with the invention is barely affected by constant shear stresses of long duration, allowing them to be adapted to industrial processes for which permanent stirring is required. For example, when the shear stress is applied at 50 $s^{-1}$ over a period of approximately 10 minutes, a decrease in the viscosity of the dextran in solution synthesized by DSR-S vardel Δ4N is observed, which is not the case for the dextrans in accordance with the invention, in particular synthesized by the recombinant DSR-OK dextransucrase as demonstrated in example 12.

In addition, the dextrans in accordance with the invention have a relatively high yield point, in particular of between 25 and 40 Pa according to the initial amount of sucrose present in the reaction medium, as presented in example 12.

The dextrans in accordance with the invention have a behavior of weak gel type. This is characterized by rheology measurements under dynamic conditions, with detection of the elastic moduli or storage modulus G' and the viscose modulus or loss modulus G". For a gel, G' is greater than G" over the frequency range studied, as visible in example 12.

Finally, the dextrans in accordance with the invention have glass transition temperatures of 95° C. for a water content of 6.6%, and of 25° C. for a water content of 12.9%. In other words, for a water content of approximately 13%, the dextrans according to the invention exhibit a rubbery state, which is flexible at temperatures greater than approximately 25° C., and are considered to be "brittle" below approximately 25° C.

The present invention also relates to a novel dextransucrase, called DSR-OK, which makes it possible to synthesize dextrans in accordance with the invention.

A subject of the present invention thus relates to a dextransucrase of which the amino acid sequence is the sequence SEQ ID NO: 1.

The genomic DNA sequence of the *Oenococcus kitaharae* DSM 17330 strain was published in 2012 under Genbank reference No. CM001398.1 (whole genome shotgun sequence) (4). In the NCBI database, the gene encoding DSR-OK is described as putative glycosyltransferase (accession number EHN59583).

The inventors have discovered, surprisingly, that this protein sequence encodes an enzyme, a dextransucrase that is very active and particularly advantageous. This result was unexpected for several reasons.

First of all, this enzyme is derived from a lactic acid bacterium, *Oenococcus kitaharae* DSM17330, isolated for the first time in 2006 in by-products from shochu distilling (3). This new species, *kitaharae*, was identified at the time as being a lactic acid bacterium belonging to the *Oenococcus* genus, but diverging from *Oenococcus oeni* in that it is non-acidophilic and does not carry out malolactic fermentation. The researchers who grew this strain on an MRS medium, i.e. a conventional medium for the growth of lactic acid bacteria, supplemented with sucrose, also came to the conclusion, in 2006, that the *Oenococcus kitaharae* DSM17330 strain does not produce dextran in the extracellular medium from sucrose. It could thus have been assumed that this glucosyltranferase is inactive on sucrose.

Finally, the sequence of DSR-OK has only a maximum identity of 58% (over 97% of its sequence) with the dextransucrase DSR-N of *Leuconostoc mesenteroides* KIBGE IB-22, the sequence of which is available in the databases under Genbank accession No. AFP53921.1. Compared with other putative sequences of glucansucrases that can be identified following bacterial genome sequencing campaigns, this percentage identity is low. Moreover, the CAZy databases, which take an inventory of all the enzymes active on sugars, does not yet make any mention of this strain and of this gene in the GH-70 family, the glucansucrase family.

Those skilled in the art were thus not led to consider this putative enzyme as a potential dextransucrase that was advantageous by virtue of its catalytic properties and the dextrans synthesized.

The exceptional properties of DSR-OK as a dextransucrase have finally been demonstrated by the inventors.

The DSR-OK dextransucrase is composed of 1484 amino acids, having the DED catalytic triad and the 4 conserved motifs usually described in the enzymes of glycoside hydrolase family 70. The conserved protein motifs of the catalytic core (I to IV) have thus been identified from position 936 to position 942 for motif I, from position 458 to position 468 for motif II, from position 495 to position 505 for motif III and from position 568 to position 582 for motif IV. In comparison with the protein sequence of the GTF-180 glucansucrase, the five structural domains conventionally described for glucansucrases (A, B, C, IV and V) (5) can be identified in the primary structure of DSR-OK (FIG. 1).

DSR-OK is a dextransucrase very specific for polymerization via glycosidic bonds of α-1,6 type, and is an excellent polymerase. Indeed, as can be seen in example 5, the chromatographic analyses carried out following a dextran synthesis from 100 g.l$^{-1}$ of sucrose show that approximately 89% of the glucosyl units derived from the substrate are used for the production of the polymer.

Figure 2:
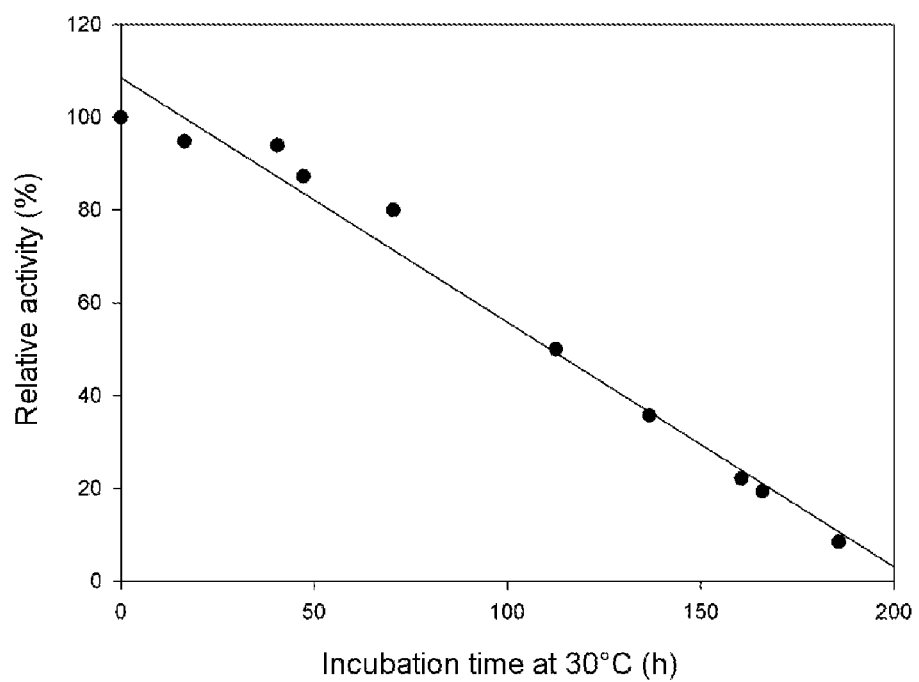

In addition, DSR-OK has an optimal operating temperature of approximately 30° C. and an optimal pH of approximately 5.75. At 30° C., this dextransucrase is stable and robust, its half-life time being approximately 111 h during characterization in crude medium, i.e. non-purified medium, as can be seen in FIG. 2. This property is particularly advantageous and rare in glucansucrases. Thus, in comparison, DSR-S vardel Δ4N, another recombinant glucansucrase, has a half-life time of only 24 h under the same conditions.

Moreover, DSR-OK follows a Michaelian mechanism, with inhibition by excess substrate, and is a very effective catalyst in comparison with other similar dextransucrases, as presented in example 8. For example, DSR-OK has an affinity constant, Km, of 8.99 mM and a catalytic constant, Kcat, of 550 s$^{-1}$ (see FIGS. 3 and 4). The enzyme thus has good affinity for the substrate (Km), of the same order of magnitude as most of the dextransucrases characterized, and has an excellent catalytic constant (kcat), rarely observed in glucansucrases. The enzyme is thus extremely efficient for catalyzing polymerization reactions from sucrose.

Figure 5:
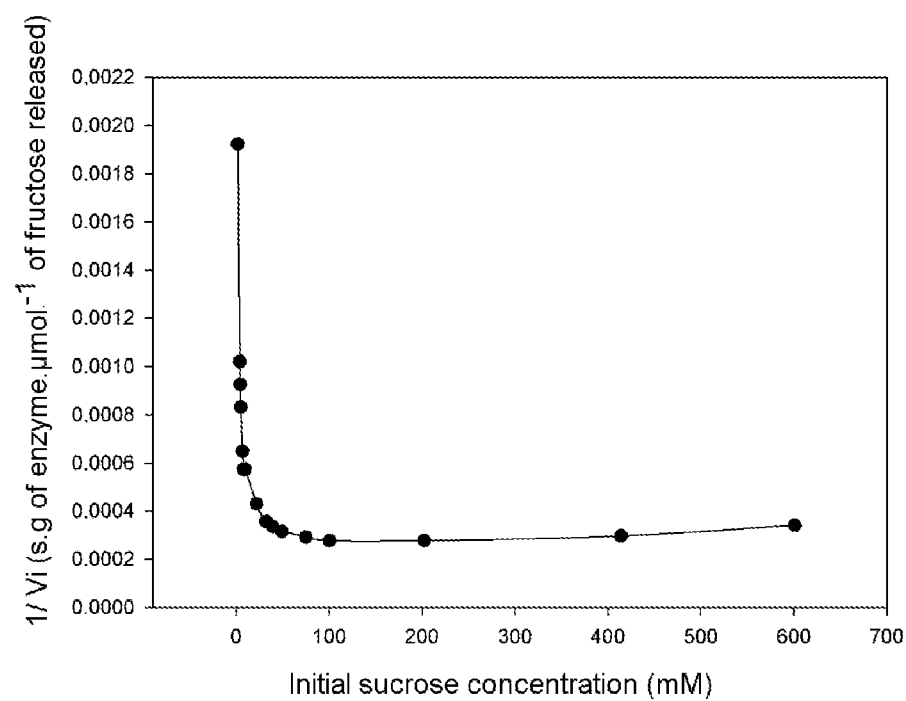

Finally, as can be seen in FIG. 5, the inhibition constant of DSR-OK comes to 1M, thereby showing that this dextransucrase is barely inhibited by excess substrate. This characteristic allows its use in processes for synthesizing dextran from very variable concentrations of initial sucrose depending on the molecular weight of the dextran targeted. Indeed, it is known that increasing the concentration of initial substrate promotes the synthesis of lower molecular weight dextrans (2).

The function-preserving variants are also included in the present application. The term "function-preserving variant" refers to a variant in which one (or more) given amino acid residue(s) in a protein has (have) been modified without however detrimentally modifying the overall conformation and the enzymatic activity of dextransucrase making it possible to synthesize dextrans in accordance with the invention. Typically, the modification may involve non-sensitive parts of the enzyme, and in particular does not involve the catalytic triad.

Thus, one particular embodiment of the invention relates to the function-preserving variants. Typically, such a function-preserving variant is a dextransucrase of which the amino acid sequence has at least 80%, preferably 85%, more preferably 90%, more preferably 95%, more preferably 98% identity over the positions ranging from 359 to 1038 on the amino acid sequence SEQ ID NO: 1, which corresponds to the domains A+B+C of the enzyme, on condition that the dextransucrase enzymatic activity, making it possible to synthesize dextrans in accordance with the invention, is maintained.

A dextransucrase according to the invention can thus be both the enzyme of sequence SEQ ID NO: 1, as previously defined, and a variant of the dextransucrase enzyme of sequence SEQ ID NO: 1, on condition that this variant preserves the function of the enzyme.

A subject of the invention thus relates to a dextransucrase having as amino acid sequence the sequence SEQ ID NO: 1, or at least 80%, preferably 85%, more preferably 90%, more preferably 95%, more preferably 98% identity with the sequence ranging from positions 359 to 1038 of the amino acid sequence SEQ ID NO: 1.

The enzymatic activity of a dextransucrase variant can be tested according to techniques known to those skilled in the art, for example using the dinitrosalicylic acid (DNS) method of Sumner and Howell (10) or by HPLC analysis.

According to one particular embodiment, a dextransucrase according to the invention can be prepared by known genetic recombination techniques.

Those skilled in the art will be able to use molecular biology techniques and will be able to choose a suitable expression system according to the techniques known thereto. Reference may be made here to example 2 hereinafter.

The term "expression system" comprises a host cell and a vector compatible under appropriate conditions, i.e. conditions which allow the expression of the protein encoded by the foreign DNA borne by the vector and introduced into the host cell. Typically, the nucleic acid sequence encoding a dextransucrase, preferably a DSR-OK dextransucrase as previously described or a function-preserving variant, can be inserted into an appropriate expression vector that will then be introduced into an appropriate prokaryotic or eukaryotic host cell.

An expression vector is typically a plasmid, a cosmid, an episome, an artificial chromosome, a phage or a viral vector.

Typically, the expression of the nucleic acids of the present invention can be carried out in prokaryotic or eukaryotic host cells. As non-limiting examples of prokaryotic host cell strains, mention may be made of strains such as *Escherichia coli*, *Bacillus subtilis*, *Salmonella typhimurium* or strains of the *Pseudomonas*, *Streptomyces* and *Staphylococcus* genera. As non-limiting examples of eukaryotic host cell strains, mention may be made with strains such as Apicomplexan (*Plasmodia*, *Toxoplasma*, *Cryptosporidia*), *Leishmania* or *Trypanosoma* parasites, or cells of yeasts such as *Saccharomyces*, for instance *Saccharomyces cerevisiae* or *pombe*, *Pichia pastoris*, etc.

Preferentially, prokaryotic host cells are used. According to one advantageous embodiment, the cells used for expressing the nucleic acids of the present invention are *Escherichia coli* and, more preferentially, the strains are chosen from TOP10, BL21AI, BL21 Star DE3 and Arctic Express DE3.

Advantageously, the dextransucrase may also comprise, at the N-terminal end, a signal sequence. This signal sequence may be one of the signal sequences known to those skilled in the art, in particular so that, when the protein is synthesized in a host cell, the dextran synthesis can be carried out extracellularly. Indeed, the DSR-OK dextransucrase does not have a signal peptide. The presence of a suitable signal peptide thus allows the dextran synthesis extracellularly. Furthermore, genetic tools are being increasingly developed for heterologous expression in GRAS (Generally Recognized As Safe) microorganisms of the *Bacillus* and *Lactococcus* genera. Thus, there are at the current time several known systems for excretion of recombinant proteins in these bacteria, that can be used in the present case by those skilled in the art.

As mentioned in example 2, the recombinant production of dextransucrase in *Escherichia coli* using the conditions described in example 2 reaches approximately 30 000 enzymatic activity units per liter of culture, which allows its use at low cost in polymer synthesis processes.

A dextransucrase according to the invention can thus be prepared by culturing host cells containing a nucleic acid sequence encoding a dextransucrase, preferably a DSR-OK dextransucrase as previously defined or a function-preserving variant, under conditions which allow the expression of a dextransucrase, and by isolating said dextransucrase from the culture medium according to techniques known to those skilled in the art.

Such dextransucrases can then be purified by any purification technique known to those skilled in the art, for example by precipitation, ion-exchange chromatography, affinity chromatography, hydrophobic exchange chromatography, gel filtration, reverse-phase HPLC chromatography, etc. According to one preferential embodiment, the dextransucrase obtained by host cell culture is purified by affinity chromatography. They can also be immobilized by techniques known to those skilled in the art, in particular for example by adsorption, formation of a covalent bond between the support and the protein, inclusion or encapsulation.

According to another embodiment, a dextransucrase according to the invention can be prepared directly by culturing the native strain *Oenococcus kitaharae*. The *Oenococcus kitaharae* strain in fact has only one dextransucrase gene encoding DSR-OK.

The invention also relates to the production of dextrans in accordance with the invention.

A subject of the invention thus relates to a process for producing dextrans in accordance with the invention, comprising the reaction of a dextransucrase of sequence SEQ ID NO: 1, or a function-preserving variant as previously described, with sucrose.

The person skilled in the art will be able to adjust the fermentation conditions to be applied in order to have optimized dextran production.

Generally, the dextransucrase must be incubated in a synthesis medium containing sucrose.

According to one particular embodiment, microorganisms secreting dextransucrase or cell extracts of microorganisms producing dextransucrase intracellularly can be cultured or used in a medium comprising sucrose, this leading to the synthesis of dextran in accordance with the invention.

As previously described, the dextran synthesis can be carried out using purified or non-purified native dextransucrase or recombinant dextransucrase.

Thus, according to another particular embodiment, a recombinant dextransucrase, preferably the DSR-OK dextransucrase or a function-preserving variant, is incubated in a synthesis medium containing sucrose.

Advantageously, the reaction is carried out at a temperature of between 20° C. and 40° C., preferably of between 25° C. and 35° C., more preferably of between 30° C. and 33° C. Typically, the reaction is carried out at a temperature of approximately 30° C.

Those skilled in the art will be able to adjust the synthesis time, in particular according to the amount of enzyme added to the reaction medium and according to the temperature. Typically, the reaction is carried out for a period of time of between 4 hours and 20 hours, preferably of between 8 hours and 16 hours, preferably for a period of time of approximately 12 hours.

Furthermore, the sucrose concentration is preferably between approximately 50 and 200 g.l$^{-1}$, preferably between approximately 50 and 150 g.l$^{-1}$. Typically, the sucrose concentration is approximately 100 gl$^{1}$. Generally, it is known that the average molar mass of the dextran synthesized will be more liable to be high when using a low initial concentration of sucrose.

Advantageously, the pH during the reaction is between approximately 5 and 6.5, preferably between 5 and 6, more preferably between 5 and 5.8. Typically, the pH during the reaction is approximately 5.75.

A subject of the invention relates to a cosmetic or food composition comprising dextrans as previously described and at least one pharmaceutically acceptable or food-grade support.

Dextrans in accordance with the invention may be used in any type of application for which its physicochemical properties are suitable, for example applications requiring high molar mass dextrans and/or a high viscosity at low shear, a shear-thinning behavior, with a viscosity that is stable over time during constant shear stresses of long duration, and having a relatively high yield point (of about 30 Pa).

Dextrans in accordance with the invention can thus be used in the oil industry or the cosmetics industry or else in the food-processing industry.

By way of nonlimiting examples, dextrans in accordance with the invention can be used for enhanced oil recovery. They can also be used in the drilling and mining fields, for example as a flocculating agent, as described in application FR 2 978 773 A. Dextrans in accordance with the invention can also be used as thickeners, gelling agents and/or texturing agents, for example as a substitute for gum Arabic, or in products such as gel products or sauces, for baked or confectionery products or for ice creams. Reference may for example be made to patent U.S. Pat. No. 6,627,235 which describes the use of high molar mass dextrans in baked products for improving the texture of the products and also their resistance to baking and to going stale.

A subject of the invention thus relates to the use of dextrans in accordance with the invention as a thickener, gelling agent and/or texturing agent.

The invention also relates to dextran hydrolysates.

The term "dextran hydrolysate" is intended to mean herein a dextran in accordance with the invention which undergoes one or more additional treatment steps capable of conferring thereon a controlled molar mass lower than the molar mass achieved according to the present invention. Such methods are known to those skilled in the art. For example, acid hydrolysis followed by fractionation, in particular by means of organic solvents, can be applied.

The invention also relates to acceptor reactions carried out using sucrose and glucooligosaccharides added to the reaction medium at the beginning of synthesis (glucose or maltose, for example). This acceptor reaction is well known to those skilled in the art for promoting the synthesis of lower molar mass dextrans from sucrose alone, and the products obtained can have applications similar to those of the dextrans obtained via hydrolysates.

The dextrans obtained, of smaller size, can thus be used in all the fields for which such a lower molar mass is appropriate, for example for pharmaceutical applications (blood plasma substitute, iron transporter or anticoagulant), for analytical applications (versatile supports for chromatography), in the medical field (blood plasma expander), etc. Reference may thus be made to the publication Vettori et al. (6).

A subject of the invention relates to a process for producing a dextran hydrolysate, in which a dextran in accordance with the invention undergoes hydrolysis and fractionation steps.

Finally, the invention relates to dextran derivatives.

The term "dextran derivative" is intended to mean herein a dextran in accordance with the invention which undergoes one or more known chemical modification steps, in particular chosen from etherification, esterification or crosslinking. It is thus possible to obtain a dextran derivative such as a crosslinked dextran, a dextran ester, for example an inorganic dextran ester (dextran phosphate, dextran sulfate) or an organic dextran ester, a dextran ether, for example a nonionic dextran ether (alkylated dextran, dextrin hydroxyalkyl ether or hydroxyalkylaryl ether, poly(ethylene glycol) alkyl dextran ether) or an ionic dextran ether (sulfopropylated dextran, carboxymethylated dextran, 2-(diethylamino) ethyl dextran). Such chemical modification techniques and also the applications for which the dextrans thus obtained are suitable, are well known to those skilled in the art. Reference may for example be made to the document Heinze et al. (7) and to the thesis by Ndegwa Henry Maina (8).

A subject of the invention thus relates to a process for modifying a dextran in accordance with the invention, in which the dextran undergoes one or more chemical modification steps.

Advantageously, a chemical modification step is chosen from etherification, esterification and crosslinking

FIGURES

FIG. 1: Diagrammatic representation of the primary structure of DSR-OK (based on the protein alignment with the GFT180 enzyme from *Lactobacillus reuteri* 180). Five domains are distinct: domain V in red, domain IV in yellow, domain B in green, domain A in blue and domain C in violet. The catalytic triad is indicated by the white letters "D", "E" and "D".

FIG. 2: Graphic representation of the relative activity of the DSR-OK dextransucrase at 30° C. as a function of time.

Figure 3:
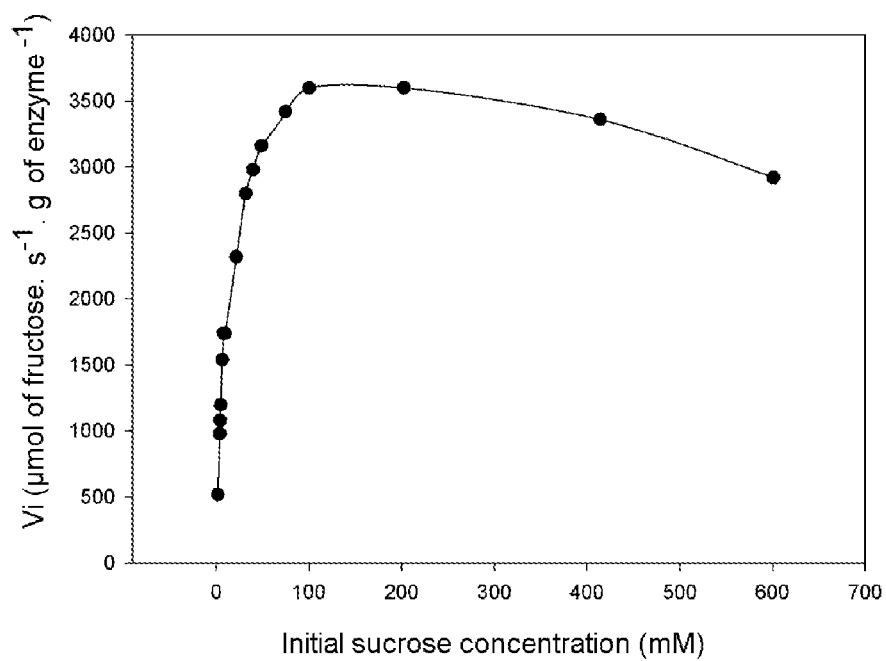

FIG. 3: Determination of the inhibition constant for inhibition by excess substrate (variation of the inverse of the initial rate as a function of the initial concentration of substrate).

Figure 4:
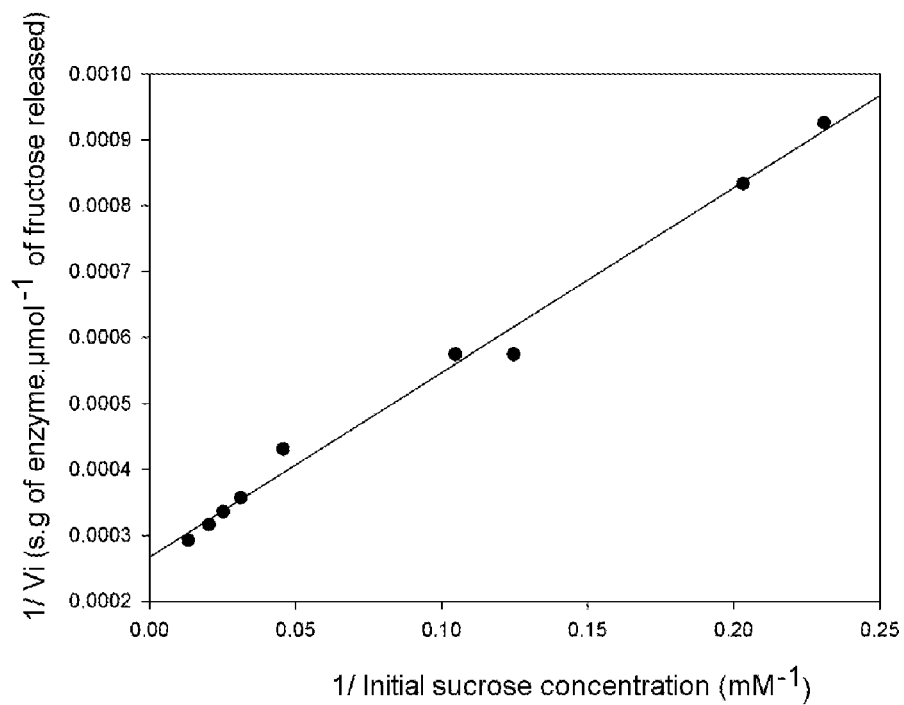

FIG. 4: Graphic Michaelis-Menten representation (variation of the initial rate of fructose production as a function of the initial concentration of substrate).

FIG. 5: Graphic Lineweaver-Burk representation (variation of the inverse of the rate as a function of the inverse of the concentration of substrate).

Figure 6:
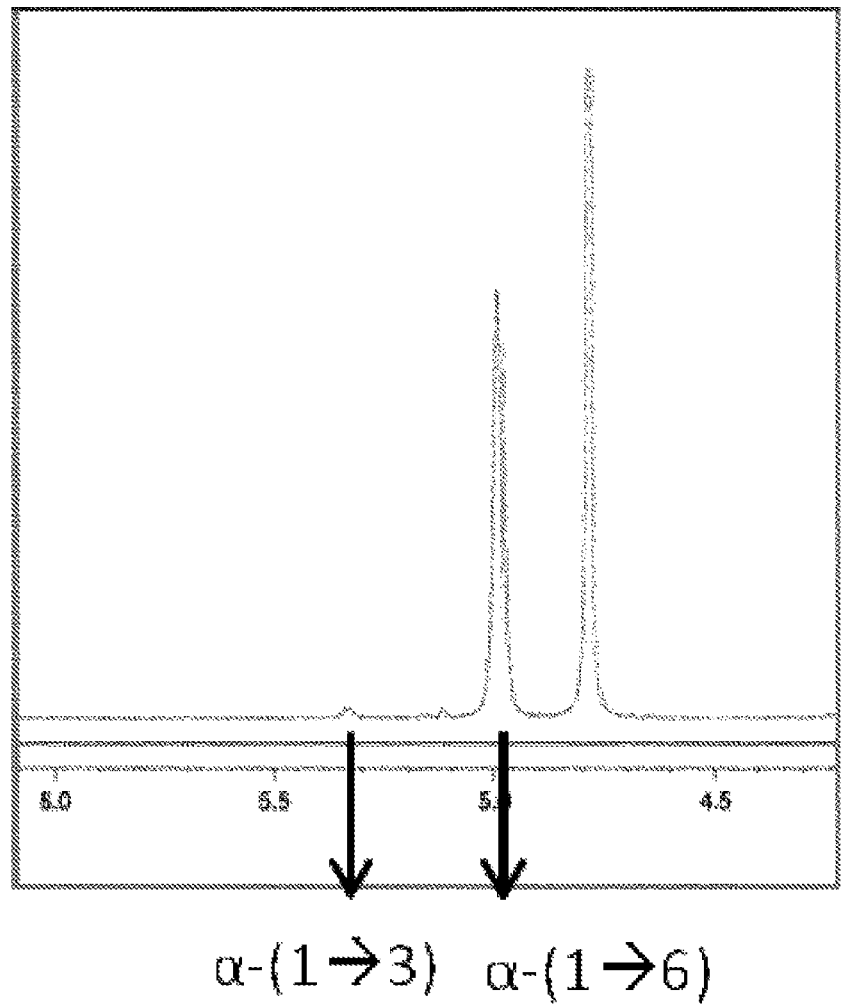

FIG. 6: Spectrum obtained by proton NMR on the dextran synthesized by recombinant DSR-OK. The arrows correspond to the α-1,3 and α-1,6 bonds.

Figure 7:
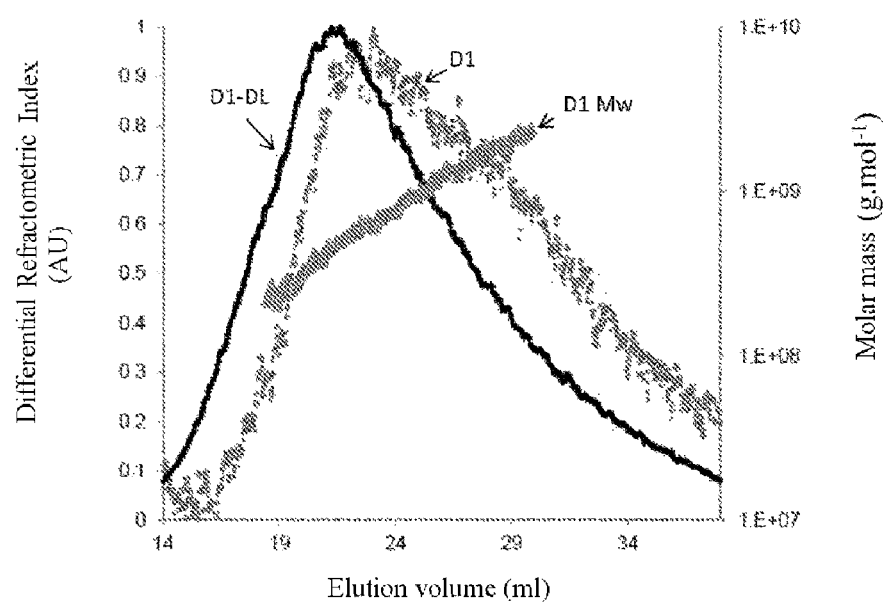

FIG. 7: Elution profile obtained by AF4-MALLS (Asymmetric Flow-Field-Flow-Fractionation-Multi-Angle Laser Light Scattering) (D1=refractometric response, D1-DL=light scattering) and molar mass distribution of the dextran produced by recombinant DSR-OK preparation (D1 Mw).

Figure 8:
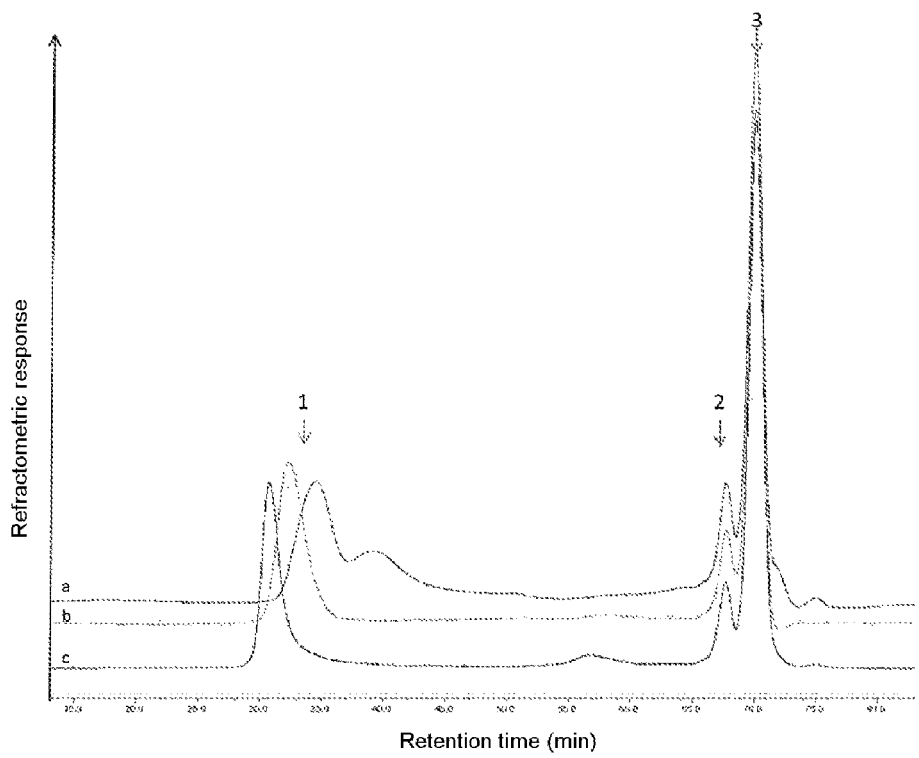

FIG. 8: Elution profiles obtained by HPSEC of the dextrans produced from 100 g.l$^{-1}$ of sucrose by (a) native DSR-S produced by *L. mesenteroides* NRRL B-512F, (b) the recombinant enzyme DSR-S vardel Δ4N and by (c) the recombinant enzyme DSR-OK. Peak 1 corresponds to the very high molar mass dextran, peak 2 to oligosaccharides with a degree of polymerization of less than 7, and peak 3 corresponds to the fructose coproduced during the reaction.

Figure 9:
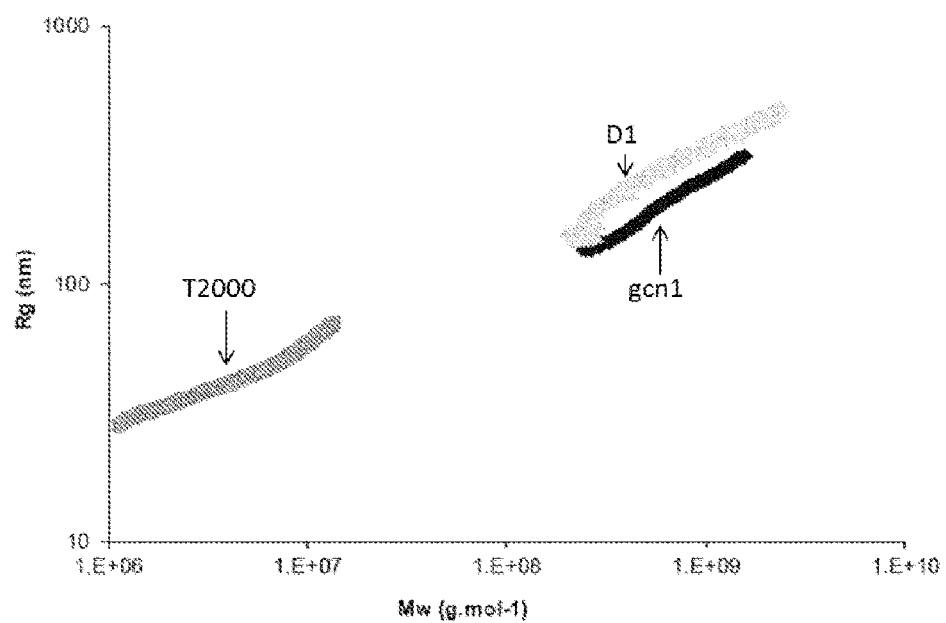

FIG. 9: Representation of the radius of gyration (in nm) as a function of the molar mass for various dextrans: gcn1 produced by a DSR-S vardel Δ4N mutant, the dextran produced by DSR-OK and a commercial dextran T2000 (Pharmacosmos) of $2 \times 10^6$ g.mol$^{-1}$.

Figure 10:
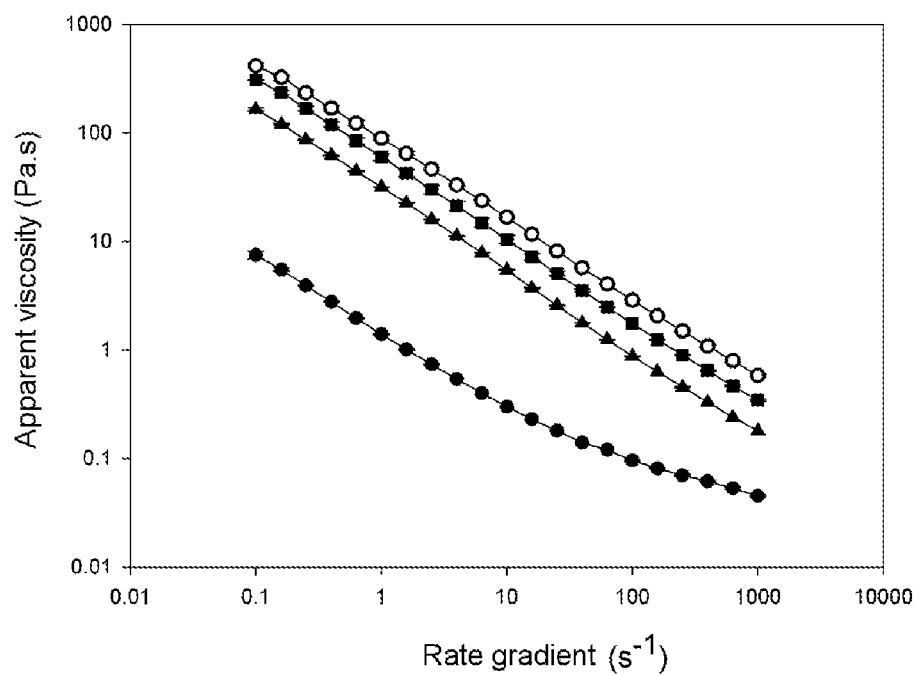

FIG. 10: Rheological behavior of the dextran as a function of the sucrose concentration by measuring the viscosity of the dextran synthesized by DSR-OK in the crude synthesis medium starting from various sucrose concentrations: 50 g.l$^{-1}$ (●), 75 g.l$^{-1}$ (▲), 100 g.l$^{-1}$ (■) and 150 g.l$^{-1}$ (○).

Figure 11:
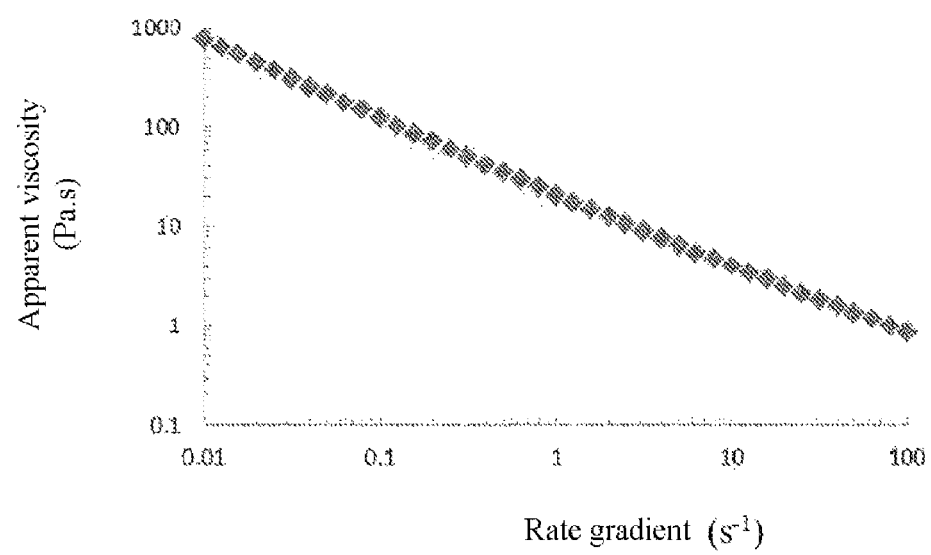

FIG. 11: Rheological behavior of the purified dextran by measuring the viscosity of the dextran synthesized by DSR-OK, purified by ethanol precipitation, and concentrated to 50 g.l$^{-1}$ in distilled water.

Figure 12:
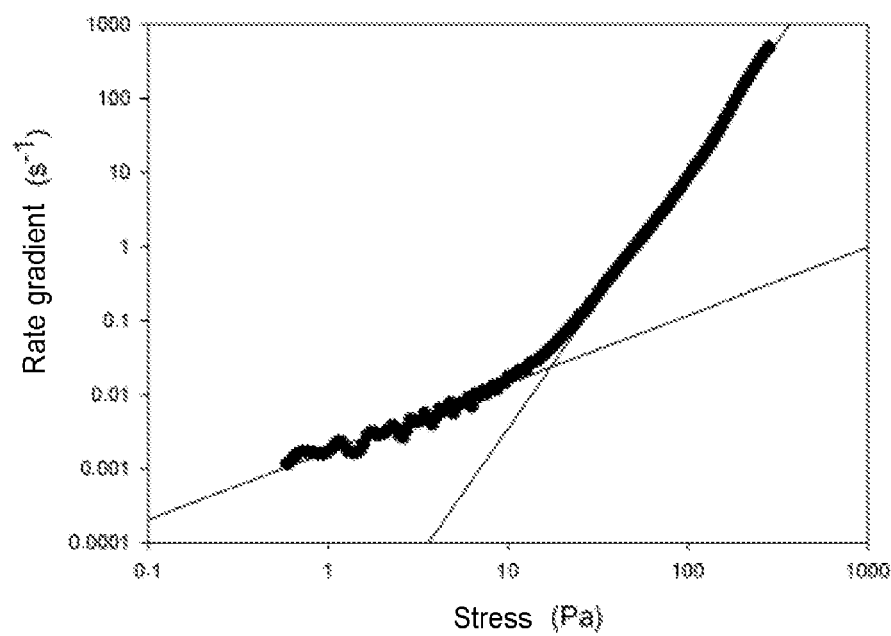

FIG. 12: Measurement of the yield point of the dextran produced by DSR-OK in the crude synthesis medium, using 100 g.l$^{-1}$ of sucrose, by graphic representation of the shear rate of the dextran at 33 g.l$^{-1}$ produced by DSR-OK as a function of the shear stress applied.

Figure 13:
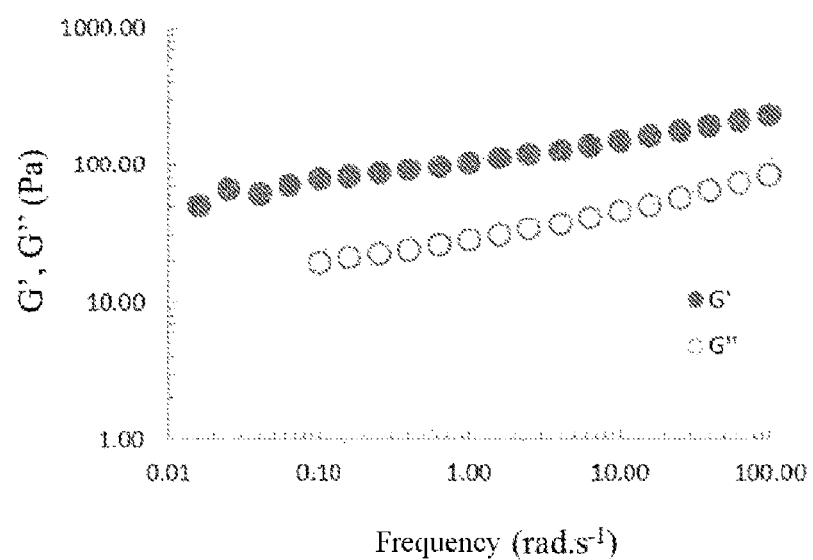

FIG. 13: Rheological behavior of the dextran produced by DSR-OK by measuring the moduli G' (●) and G" (○) by frequency scanning under oscillatory conditions (oscillations between $10^{-2}$ and $10^2$ rad.s$^{-1}$): behavior of gel type G'>G".

Figure 14:
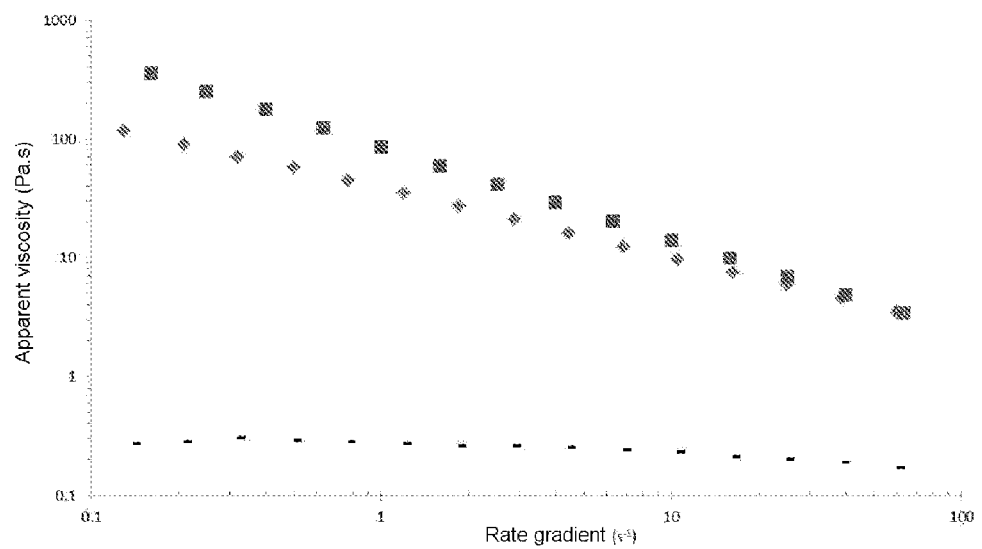

FIG. 14: Rheological behavior of various dextrans by measuring the viscosity as a function of the shear stress of dextran produced in the presence of 100 g.l$^{-1}$ of sucrose, by the recombinant DSR-OK (■), by the native DSR-S derived from *L. mesenteroides* NRRL B-512F (-), and by the DSR-S vardel D4N (◇).

Figure 15:
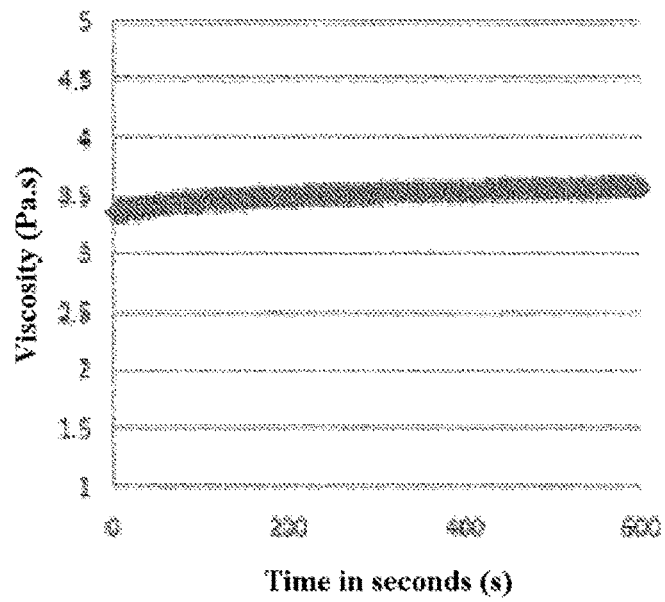
Figure 15:
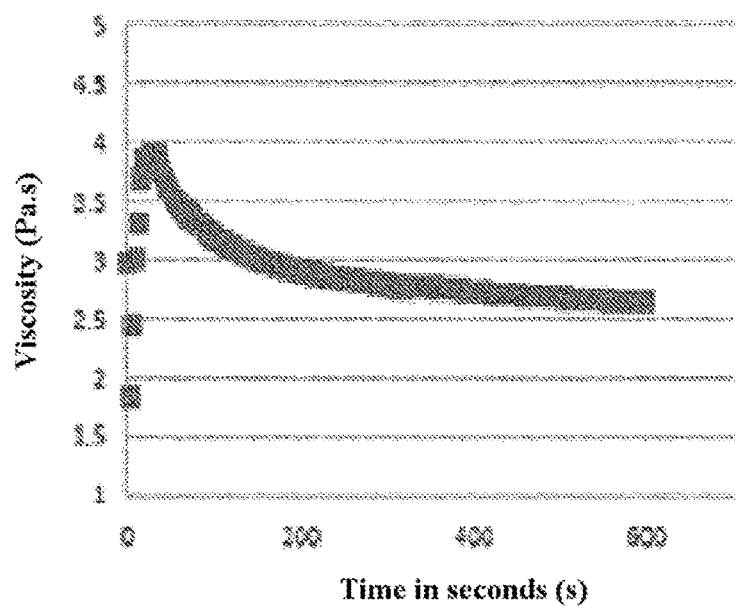

FIG. 15: Evolution of the apparent viscosity of the dextrans in their crude synthesis medium, synthesized starting from 100 g.l$^{-1}$ of sucrose. A: by recombinant DSR-OK and B: by DSR-S vardel D4N at a constant shear stress of 50 s$^{-1}$, at 20° C. and ambient atmospheric pressure.

EXAMPLES

Example 1

Identification of the Dsrok Gene in the *Oenococcus kitaharae* DSM 17330 Genome and Analysis of the Primary Structure of the Corresponding Protein The dsrok gene was identified in the genome of *Oenococcus kitaharae* DSM 17330 (available in the NCBI database under reference number NZ_CM001398) by nucleotide blast against a database consisting of glucansucrase nucleotide sequences listed in glycoside hydrolase family 70 according to CAZY (Carbohydrate Active enZYme database, www.cazy.org/GH70_all.html).

The gene was translated into protein sequence using the software available online, Transeq from EMBOSS (www.ebi.ac.uk/Tools/st/emboss_transeq/).

The absence of signal peptide was predicted by the SignalP server 4.1 software (www.cbs.dtu.dk/services/SignalP/).

Multiple protein alignments (with the overall alignment software ClustalW2, available online, www.ebi.ac.uk/Tools/msa/clustalw2/) with other characterized glucansucrases made it possible to identify the conserved motifs of the catalytic core of DSR-OK, and to cut the enzyme up into various protein domains (A, B, C, IV and V).

The various identity and similarity percentages between protein sequences, indicated in the preliminary sheet for the invention, were calculated with the BlastP tool (protein-protein Blast) from the NCBI, available online and using the default parameters proposed by the site.

Example 2

Cloning and Heterologous Expression of the Protein *Escherichia coli*

The dsrok gene was first of all amplified by PCR, from the genomic DNA of the *Oenococcus kitaharae* DSM 17330 strain, using the two primers presented in table 1.

TABLE 1

| Primer | Sequence (5' to 3') |
|---|---|
| Forward primer | CACCATGATGGCGACCGGCTC (SEQ ID NO: 2) |
| Reverse primer | GAGGATTTGACCGTTTCCAAACTTATCG (SEQ ID NO: 3) |

The addition of the 4 bases, CACC, in the 5' position of the forward primer allowed the correct insertion of the PCR fragment into the entry vector pENTR/D/TOPO (Life Technologies), in order to subsequently perform a cloning using the Gateway technology.

A positive entry clone (entry vector containing the PCR fragment in the desired sense) was selected and recombined with the destination vector pET-53-DEST (Novagen) using the LR clonase enzyme mix II (Life Technologies). The positive recombinant clones were selected and analyzed by restriction. The absence of mutation in the plasmids was confirmed by sequencing (GATC).

For the production of the recombinant enzyme, *Escherichia coli* BL21 star DE3 cells were transformed with the pET-53/DSR-OK plasmid constructed as indicated previously. 300 μl of the transformation mix were inoculated into 30 ml of LB (Lysogeny Broth) medium, supplemented with 100 μg.ml$^{-1}$ of ampicillin, and incubated overnight at 37° C. in order to prepare a preculture.

Cultures of 1 L in modified ZYM5052 medium (1% glycerol, 0% glucose, 1% lactose, Studier, 2005) were thus inoculated at an initial optical density OD 600 nm of 0.05 using the preculture from the day before, then incubated for 24 hours at 23° C. and 150 rpm. At the end of fermentation, the culture media are centrifuged (15 min, 6500 rpm, 4° C.)

and the pellets are concentrated to an OD of 80 in 50 mM of sodium acetate buffer, pH 5.75.

In order to obtain the recombinant enzyme (produced intracellularly by *Escherichia coli*), the cells are ruptured with ultrasound according to the following protocol: 5 cycles of 20 seconds at 30% of the maximum power of the probe, under cold conditions, with 4 minutes of rest in ice between each cycle. The sonication supernatant (containing the soluble recombinant enzyme) is then recovered after 30 minutes of centrifugation (10 000 rpm, 10° C.) and stored at 4° C.

The recombinant production of dextransucrase in *Escherichia coli* using the conditions described herein achieves approximately 30 000 units of enzymatic activity per liter of culture, which allows its use at low cost in polymer synthesis processes.

Example 3

Method of Determining the Enzymatic Activity of the DSR-OK Enzyme

One glucansucrase enzymatic unit represents the amount of enzyme which releases one µmol of fructose per minute, at 30° C., from 100 g.l$^{-1}$ of sucrose in 50 mM of sodium acetate buffer, at pH 5.75.

The activity is determined by measuring the initial rate of production of the reducing sugars using the dinitrosalicylic acid (DNS) method. During a time course, 100 µl of reaction medium are removed and the reaction is stopped by adding an equivalent volume of DNS. The samples are then heated for 5 min at 95° C., cooled in ice, and diluted 50/50 in water, and the absorbance is read at 540 nm. A standard range of from 0 to 2 g.l$^{-1}$ of fructose makes it possible to establish the link between the absorbance value and concentration of reducing sugars.

Example 4

Determination of the Optimal Working Conditions for the DSR-OK Enzyme

The optimal temperature value was determined by measuring the activity of the crude enzymatic extract at various temperatures (between 23 and 40° C.) using 100 g.l$^{-1}$ of sucrose in 50 mM of sodium acetate buffer, to pH 5.75.

The recombinant DSR-OK dextransucrase enzyme has an optimal temperature of 30° C.

The effect of the pH on the enzymatic activity of the crude enzymatic extract is measured at 30° C. using 100 g.l$^{-1}$ of sucrose, in 50 mM of citrate phosphate buffer, for pH values of between 3.5 and 8 (intervals of 0.5).

The recombinant DSR-OK dextransucrase enzyme has an optimal pH of between 5 and 5.8.

Example 5

Determination of the Production Yields and of the Polymerase Activity of the Recombinant DSR-OK Dextransucrase Enzyme The production yields are determined by anion exchange chromatography (HPAEC-PAD, High Performance Anion Exchange Chromatography with Pulsed Amperometric Detection), for an enzymatic reaction at 1 U.ml$^{-1}$ of DSR-OK, using 100 g.l$^{-1}$ of sucrose in 50 mM of sodium acetate buffer, pH 5.75. The sugars, glucose, fructose, leucrose and sucrose are separated on a Dionex CarboPac PA-100 column by means of a sodium acetate gradient of from 6 to 500 mM over the course of 36 min, containing 150 mM of sodium hydroxide. Standard ranges of 5, 10, 15 and 20 mg.kg$^{-1}$ of these sugars are prepared and enable their quantification.

The production yields, that is to say the share of glucose derived from the sucrose, that is incorporated into the formation of free glucose, of leucrose and of dextran, are calculated as follows:

$$\% G \text{ glucose} = \frac{([\text{Glucose}]tf - [\text{Glucose}]t0) \times 342}{([\text{Sucrose}]t0 - [\text{Sucrose}]tf) \times 180} \times 100$$

$$\% G \text{ leucrose} = \frac{([\text{Leucrose}]tf - [\text{Leucrose}]t0)}{([\text{Sucrose}]t0 - [\text{Sucrose}]tf)} \times 100$$

The analysis of the reaction products by size exclusion chromatography (HPSEC) shows that there is synthesis of only glucose, leucrose and very high molecular weight dextran. As a consequence of recurring problems of clogging of the columns during the analysis with this polymer, direct quantification of the very high molecular weight dextran cannot be carried out. The percentage of glycosyl units incorporated in the dextran synthesis was deduced from the HPAEC-PAD analyses as follows:

%$G$ dextran=100%−(%$G$ glucose+%$G$ leucrose)

It was demonstrated here that the enzyme is an excellent polymerase. Indeed, the chromatographic analyses (HPAEC-PAD and HPSEC-RI) carried out following a synthesis of dextran from 100 g.l$^{-1}$ of sucrose show that approximately 89% (more specifically, 86% ±5%) of the glycosyl units derived from the substrate are used for the production of the polymer under the standard production conditions (100 g.l$^{-1}$ of sucrose, at 30° C. and at pH 5.75).

Only 2% and 9% of these units are lost by incorporation into the synthesis of free glucose and of leucrose, respectively.

Example 6

Study of the Stability of the DSR-OK Recombinant Enzyme

In order to study the stability of DSR-OK at 30° C., the enzyme (purified or nonpurified) is placed at 30° C., initially at 40 U.ml$^{-1}$, in 50 mM of sodium acetate buffer, pH 5.75. The residual activity is measured, at regular intervals, starting from 100 g.l$^{-1}$ of sucrose, in 50 mM of sodium acetate buffer, pH 5.75, until complete denaturation of the protein. The half-life time corresponds to the time at which the enzyme has lost half its initial enzymatic activity.

As can be seen in FIG. 2, the half-life time of the DSR-OK enzyme at 30° C. is 111 h±10 h during a characterization in crude (nonpurified) medium. The DSR-OK enzyme is thus very stable, which is a particularly advantageous property for a glucansucrase of glycoside hydrolase family 70.

In comparison, DSR-S vardel Δ4N, another recombinant glucansucrase, has a half-life time of only 24 h under the same conditions.

Example 7

Purification of the DSR-OK Recombinant Enzyme by Affinity Chromatography

The DSR-OK recombinant enzyme produced in *Escherichia coli* is fused to two purification tags, 6×His and Strep Tag II, at the N- and C-terminal ends respectively, in order to allow affinity purification. A double purification on a StrepTactin column (affinity for the Strep Tag II tag) proved to be the method that was the most efficient and of excellent quality.

The enzymatic purifications are carried out on the ÄKTAxpress system from GE Healthcare, in a chamber at 8° C. 10 ml of enzymatic extract containing the tagged DSR-OK protein are injected into a 5 ml Strep Tactin Sepharose High Performance™ column (GE Healthcare), preequilibrated with 1× PBS buffer, 280 mM NaCl, pH 7.4. After one hour of binding in a closed circuit, the elution is carried out, at 4 ml.min$^{-1}$, by means of a D-desthiobiotin gradient of from 0.05 to 2.5 mM in binding buffer (1× PBS, 280 mM NaCl, pH 7.4) on 20 column volumes. The purified fraction is desalted on a 10 DG column (Biorad) preequilibrated with 50 mM of sodium acetate buffer, pH 5.75, 0.05 g.l$^{-1}$ CaCl$_2$, 0.1% Tween80. In order to improve the purification factor and the quality of the pure enzymatic preparation, the extract previously obtained is again purified according to these same conditions.

The protein concentrations measured at 280 nm in a Nanodrop 1000 3.7.1 spectrophotometer from Thermo Scientific, by setting the molar extinction coefficient of the DSR-OK enzyme at 224160 M$^{-1}$.cm$^{-1}$ and its molecular weight at 165124 Da (predicted by the Expasy ProtParam program available online).

Example 8

Determination of the Kinetic Parameters of the Recombinant DSR-OK Dextransucrase Enzyme The kinetic parameters (Vm, Km and Kcat) were determined at 30° C., in 50 mM of sodium acetate buffer, pH 5.75, supplemented with 250 mg.l$^{-1}$ of BSA. The initial rates are measured for sucrose concentrations ranging from 2 to 600 mM, using the purified enzyme at a final concentration of 1 U.ml$^{-1}$. Samples are taken at regular intervals, and the enzymatic reaction is stopped by heating at 95° C. for 5 min.

The samples are then analyzed by high performance liquid chromatography (HPLC) on an Aminex Biorad HPX-87K column (300×7.8 mm, Biorad). The column oven temperature is maintained at 65° C. and ultrapure water is used as eluent at a flow rate of 0.6 ml.min$^{-1}$. Standard ranges of 5, 10, 15 and 20 g.kg$^{-1}$ of sucrose, leucrose, glucose and fructose are prepared in order to allow quantification of various sugars. The detection is carried out by refractometry.

Since DSR-OK is a Michaelian enzyme, the kinetic parameters Vm and Km are determined from the graphic Lineweaver and Burk representation, according to the equation $$\frac{1}{vi} = \left(\frac{Km}{V\max} \times \frac{1}{[S]}\right) + \frac{1}{V\max}$$

where [S] represents the initial concentration of sucrose and vi represents the initial rate.

The kinetic parameters of the enzyme were determined in 50 mM of sodium acetate buffer, pH 5.75, in the presence of BSA (250 mg.l$^{-1}$) and at 30° C.

It was thus demonstrated that DSR-OK, which follows a Michaelian mechanism with inhibition by excess substrate, is a very effective catalyst with an affinity constant Km of 9 mM±1 mM and a catalytic constant Kcat of 550 s$^{-1}$ (FIGS. 3 and 4).

These values are close to those of the DSR-S vardel Δ4N dextransucrase which is one of the most effective enzymes among the characterized glucansucrases of glycoside hydrolase family 70 (Km of 7.5 mM and Kcat of 584 s$^{-1}$).

However, DSR-OK differs from the DSR-S vardel Δ4N dextransucrase in that it is much less inhibited by excess substrate. Indeed, as can be seen in FIG. 5, its inhibition constant only comes to 1M compared with 0.326M for DSR-S vardel Δ4N.

Example 9

Synthesis of Dextran by the Recombinant DSR-OK Dextransucrase

The dextran syntheses are carried out starting from variable concentrations of sucrose (generally 100 g.l$^{-1}$), at 30° C. in 50 mM of sodium acetate buffer, pH 5.75, and using 1 U.ml$^{-1}$ of enzyme over a period of time of 15 h. For most of the analyses, the polymer was purified by two precipitations with 50% ethanol, followed by two washes and by resuspension in ultrapure water before being lyophilized.

Example 10

Analysis of the Nature of the Bonds of the Dextran Produced by the Recombinant DSR-OK Dextransucrase After lyophilization, 20 mg of purified dextran are diluted in 0.5 ml of deuterated water and analyzed by proton NMR with the Bruker Avance spectrometer (500 MHz). The spectra are then processed and interpreted with the TOPSPIN 3.0 software.

It was thus demonstrated by the NMR analyses that the product synthesized from 100 g.l$^{-1}$ of sucrose, at 30° C., pH 5.75, is a polymer of glycosyl units which are 97.6% (±0.2%) α-1,6 linked and 2.4% α-1,3 linked, as shown in FIG. 6.

It is thus a virtually linear dextran, and this further demonstrates that the DSR-OK dextransucrase is a dextransucrase that is very specific for polymerization via glycosidic bonds of α-1,6 type.

Example 11

Determination of the Macromolecular Characteristics of the Dextran Produced by the Recombinant DSR-OK Dextransucrase The number-average and weight-average molar mass and the structure of the dextran synthesized by DSR-OK were then analyzed by AFFFF-MALLS (Asymmetric Flow-Field-Flow-Fractionation-Multi-Angle Laser Light Scattering), using the crude synthesis media under the production conditions described in example 9.

The samples were diluted 500 times, in water containing 0.02% of sodium azide, and filtered on a 0.45 μm Durapore membrane, before injection (filtration yield>90%). The operating mode is the same as that used to characterize the high molar mass dextrans synthesized by DSR Δ4N variants (9). Thus, the samples are injected at 0.2 ml.min$^{-1}$ over a period of time of 300 s with a cross flow of 1 ml.min$^{-1}$. Once the injection is complete, a relaxation time of 60 seconds is imposed on the samples. The elution is carried out under an entrainment flow of 0.84 ml.min$^{-1}$, at a constant cross flow of 0.1 ml.min$^{-1}$ for 3125 seconds, at ambient temperature. The molar mass values (M$_i$) and the radius of gyration values (R$_{Gi}$,) are determined with the ASTRA software, version 5.3.2.13 (Wyatt Technology).

At each time interval (i), the refractometric response makes it possible to determine the concentration $C_i$. The molar mass and the radius of gyration are determined by extrapolation from the relationship of the light scattering at zero angle, by means of a Berry diagram according to:

$$\sqrt{\left(\frac{K_C}{R_\theta}\right)} = \sqrt{\frac{1}{M_i}\left(1 + \frac{16\pi^2 n^2}{3\lambda^2}R_{Gi}^2 \sin^2(\theta/2)\right)}$$

where K is the optical constant, $R_\theta$ is the Rayleigh ratio, $\lambda$ is the wavelength of the incident laser beam, n is the refractive index of the light and $\theta$ is the angle of observation.

The ASTRA software directly calculates the weight-average molar masses ($M_w$) and number-average molar masses ($M_n$), and also the z-average radius of gyration ($R_{Gz}$) according to the following relationships:

$$M_n = \frac{\Sigma_i c_i}{\Sigma_i \frac{c_i}{M_i}}$$

$$M_w = \frac{\Sigma_i c_i M_i}{\Sigma_i c_i}$$

$$R_{Gz}^2 = \frac{\Sigma_i c_i M_i R_{Gi}^2}{\Sigma_i c_i M_i}$$

The $M_w/M_n$ ratio represents the dispersity index $D_i$.

The density ($d_{Gapp}$) is calculated from the following equation:

$$d_{Gapp} = \frac{M_w}{\left(\frac{4\pi}{3}\right) \times R_{Gw}^3}$$

where $R_{Gw}$ represents the weight-average radius of gyration.

The hydrodynamic coefficient, $\upsilon_G$, is determined from the graphic representation of the radius of gyration ($R_{Gi}$) as a function of the molar mass ($M_i$) and according to the equation:

$$R_{Gi} = K_G \cdot M_i^{\upsilon_G}$$

where $K_G$ is a constant.

The value of the branching parameter $g_M$ is calculated according to the following relationship:

$$g_M = \frac{\overline{R}_{Gw(br)}^2}{\overline{R}_{Gw(lin)}^2}$$

where $R_{Gw(br)}$ and $R_{Gw(lin)}$ represent the weight-average radii of gyration of the branched polymer of its linear equivalent of the same chemical nature and of the same molar mass.

It was thus demonstrated by the analysis of the macromolecular characteristics that the dextran has a very high weight-average molar mass $M_w$ of approximately $1.01 \times 10^9$ g.mol$^{-1}$ ($\pm 0.3 \times 10^9$ g.mol$^{-1}$), as can be seen in FIG. 7.

The number-average molar mass is also high, namely $M_n = 5.5 \times 10^8$ g.mol$^{-1}$ ($\pm 1.6 \times 10^8$ g.mol$^{-1}$).

The dispersity index $D_i$ of the dextran produced by DSR-OK is thus approximately 1.8, which represents a very low index compared with the dextrans produced until now.

For example, in comparison with the dextran produced by the historic strain *L. mesenteroides* NRRL B-512F, and with the dextran produced by the DSR-S vardel Δ4N recombinant enzyme, the dextran produced by the DSR-OK dextransucrase is larger in size, and is much less polydisperse than the native dextran produced by the *L. mesenteroides* NRRL B-512F strain.

The radius of gyration of the polymer is also extremely high, about 370 nm (FIG. 9). The hydrodynamic coefficient, that is to say the slope of the graph representing the radius of gyration as a function of the molar mass (FIG. 9), is 0.48. This value shows that it is a virtually linear polymer, with very little branching.

Table 2 reiterates the main macromolecular characteristics of the dextran produced by recombinant DSR-OK.

TABLE 2

| Characteristic | Value |
| --- | --- |
| $M_w$ (weight-average molar mass) | $1 \times 10^9$ g · mol$^{-1}$ ± 0.3 × 10$^9$ g · mol$^{-1}$ |
| $M_n$ (number-average molar mass) | $5.5 \times 10^8$ g · mol$^{-1}$ ± 1.6 × 10$^8$ g · mol$^{-1}$ |
| $D_i = M_w/M_n$ (dispersity index) | 1.8 ± 0.3 |
| $R_{Gz}$ (z-average radius of gyration) | 370 nm ± 18.5 nm |
| $d_{Gapp}$ (apparent density) | 8.2 g · mol$^{-1}$·nm$^3$ ± 2.2 g · mol$^{-1}$·nm$^3$ |
| $\upsilon_G$ (hydrodynamic coefficient) | 0.48 ± 0.02 |
| $g_M$ (average branching parameter) | 0.0158 ± 0.004 |

Example 12

Analysis of the Rheological Behavior of the Dextran Produced by the Recombinant DSR-OK Dextransucrase Flow Curve and Determination of the Yield Point of the Dextran in its Crude Synthesis Medium Starting from Various Sucrose Concentrations The syntheses are carried out in a total volume of 20 ml, starting from various initial concentrations of sucrose (50, 75, 100 and 150 g.l$^{-1}$), in 50 mM of sodium acetate buffer, pH 5.75, at 1 U.ml$^{-1}$ of enzyme. The temperature and the stirring are set at 30° C. and at 60 rpm. The enzymatic reaction is carried out over a period of time of 15 hours.

The rheological analyses of the dextran (in its crude synthesis medium) are carried out on the Haake Mars III rheometer from Thermo Scientific, controlled by the Haake RheoWin 4 software. All the measurements are determined using a plate-plate geometry (diameter of 35 mm), with a gap of 0.5 mm, at 20° C. (peltier MTMC MarsIII) and at atmospheric pressure.

The flow curves are obtained by varying the rate gradient from 10$^{-1}$ to 10$^3$s$^{-1}$. The yield point values are determined from the graphic representation plotting the values of the stress as a function of the rate gradient. The yield point is determined by the stress obtained at the lowest shear rate (tending toward a plateau).

Viscosity Curve and Viscoelastic Measurements of the Purified Dextran

The polymer, purified by means of two ethanol precipitations and lyophilized, is resuspended at 50 g.l$^{-1}$ in distilled water and dissolved overnight at 25° C., with gentle stirring. The rheological properties are measured with an imposed-strain rheometer (Ares, TA.) using a cone-plate geometry (diameter of 5 cm, cone angle of 0.05 rad) at 20° C. and at atmospheric pressure. The flow curve is determined by varying the rate gradient from 10$^{-2}$ to 10$^2$s$^{-1}$. The mechanical spectra (moduli G' and G" as a function of frequency) are determined in dynamic regime, by varying the frequency from $10^{-2}$ to $10^2$ rad.s$^{-1}$, at an imposed strain amplitude located in the linear viscoelasticity range.

It is observed that the dextran polymer is very viscous to the naked eye and that it is necessary to apply a force in order for it to flow.

The flow curves determined on the basis of the crude synthesis medium for various initial concentrations of sucrose (50, 75, 100, and 150 g.l$^{-1}$) are presented in FIG. 10 and the flow curves determined on the basis of polymer purified by alcohol precipitation and prepared at a concentration of 5% (weight/volume) in distilled water are presented in FIG. 11.

In both cases, the dynamic viscosity of the solution is very high for low shear rates (of about 100 Pa.s at 0.1 s$^{-1}$. FIGS. 10 and 11). The polymer adopts a behavior of shear-thinning or pseudoplastic type, i.e. its dynamic viscosity decreases when the rate gradient (or shear rate) increases.

As can be seen in FIG. 14, the dextran produced by the DSR-OK dextransucrase has a viscosity approximately 500 times higher than the native dextran produced by *L. mesenteroides* NRRL B-512F for low applied shear stresses. In addition, the native dextran exhibits Newtonian behavior, unlike the dextrans produced by DSR-OK or DSR-S vardel Δ4N, which are shear-thinning.

Furthermore, the dextran in solution has a yield point. Thus, yield points of 26 Pa and 38 Pa were measured for the dextran in the crude synthesis medium using 100 g.l$^{-1}$ and 200 g.l$^{-1}$ of sucrose respectively (FIG. 12).

In comparison, the dextran of the synthesis medium produced by the DSR-S vardel Δ4N recombinant enzyme using 100 g.l$^{-1}$ has a yield point of 12 Pa.

Low dextran concentrations could be used for products requiring a yield point, for example as a replacement for xanthan gum solution or guar solution, used as thickeners and having yield points at 10 g.l$^{-1}$ of 7 and 4 Pa, respectively. The dextran in accordance with the present invention can thus be used in products of toothpaste, sauce, etc. type.

The frequency scanning tests, under oscillation conditions, indicate moreover that the polymer is a weak gel. This is because, as can be seen in FIG. 13, the elastic modulus G' is greater than the viscous modulus G" in the range of frequencies tested, from $10^{-2}$ to $10^2$ rad.s$^{-1}$.

Finally, it is noted that the viscosity of the polymer produced by DSR-OK remains stable when constant shear stresses of long duration are applied, while the viscosity of the polymer produced by DSR-S vadel Δ4N decreases under the same conditions (FIG. 15). The dextran in accordance with the present invention can thus be used in industrial processes for which constant stirring is required.

Example 13

Determination of the Glass Transition Temperature and of the Water Content of the Dextran Produced by the Recombinant DSR-OK Dextransucrase The polymer purified by means of two ethanol precipitations and lyophilized is equilibrated at 57% and at 43% relative humidity by placing it under vacuum in the presence of saturated solutions of NaBr and of $K_2CO_3$ at ambient temperature for one week. The glass transition temperatures ($T_g$) are determined by means of a differential scanning calorimetry system, DSC Q100 (TA Instruments, France). The device is calibrated with indium. Measurements are carried out on 2 to 30 mg of sample using sealed aluminum capsules (TA Instruments, Guyancourt, France), heated from 0 to 120° C. at 3° C.min$^{-1}$. Two heating scans were carried out, separated by a phase of cooling down to 0° C. at 10° C. min$^{-1}$, making it possible to prevent against any signature due to aging of the sample. An empty capsule is used as reference. The glass transition temperature ($T_g$) is taken at the inflection point of the change in heat capacity.

The water content is determined after each calorimetric measurement by thermogravimetric analysis (TGA) using a TGA2050 system (T.A. Instruments, New Castle, Del., U.S.A.). The water content corresponds to the weight loss when the sample is heated up to 130° C. at 10° C. min$^{-1}$ and then maintained at this temperature for 40 min.

The DSC (Differential Scanning calorimetry) analyses thus made it possible to determine glass transition temperatures of 95° C. (±1° C.) for a water content of 6.6%, and of 25° C. (±1° C.) for a water content of 12.9%.

For a water content of approximately 13%, the polymer will thus exhibit a rubbery state at temperatures above 25° C. and will be considered to be "brittle" below 25° C.

REFERENCES (1) Characterization of *Leuconostoc mesenteroides* NRRL B-512F dextransucrase (DSRS) and identification of amino-acid residues playing a key role in enzyme activity, Monchois et al., Applied Microbiology and Biotechnology, October 1997, vol. 48, Issue 4, 465-472

(2) High-level production and purification of a fully active recombinant dextransucrase from *Leuconostoc mesenteroides* NRRL B-512F, Moulis and al, FEMS Microbiology Letters, August 2006, vol. 261, Issue 2, 203-210

(3) *Functional Divergence in the Genus Oenococcus as Predicted by Genome Sequencing of the Newly-Described Species, Oenococcus kitaharae*, Borneman and al, PloS ONE, January 2012, vol. 7, Issue 1

(4) *Oenococcus kitaharae sp. nov., a non-acidophilic and non-malolacfic-fermenting oenococcus* isolated from a composting distilled shochu residue, Akihito Endo and Sanae Okada, International Journal of Systematic and Evolutionary Microbiology (2006), 56, 2345-2348

(5) Glucansucrases: Three-dimensional structures, reactions, mechanism, alpha-glucan analysis and their implications in biotechnology and food applications Lemhuis et al., Journal of Biotechnology, January 2013, vol. 163, Issue 2, 250-272

(6) *Dextran: effect of process parameters on production, purification and molecular weight and recent applications*, Vettori et al., Diálogos & Ciência, ISSN 1678-0493, no 31, September 2012

(7) Functional Polymers Based on Dextran, Thomas Heinze, Tim Liebert, Brigitte Heublein, Stephanie Hornig, Adv Polym Sci (2006) 205: 199-291, DOI 10.1007/12_100.

(8) Structure and macromolecular properties of *Weissella confusa* and *Leuconostoc citreum* dextrans with a potential application in sourdough, Ndegwa Henry Maina, 1 Jun. 2012, University of Helsinki, Department of Food and Environmental Sciences, Chemistry and Biochemistry Division.

(9) Structure and Property Engineering of alpha-D-Glucans Synthesized by Dextransucrase Mutants, Irague and al, BioMacromolecules, 2012, vol. 13, Issue 1, 187-195.

(10) A method for determination of invertase activity, Sumner & Howell, Journal of biological chemistry, 1935, vol. 108, Issue 51

(11) Online Determination of Structural Properties and Observation of Deviations from Power Law Behavior, Rolland-Sabaté et al, Biomacromolecules, 2008, vol. 9, 1719-1730.

The invention claimed is:

1. A process for producing dextrans having a weight-average molar mass $M_w$, at least equal to $0.7 \times 10^9$ g.mol$^{-1}$, and a dispersity index $D_i$ of between 1.3 and 3, wherein α-1,6 glucosidic bonds in the dextrans comprise between 95% and 99% of glucosidic bonds, the process comprising reacting sucrose with a dextransucrase that comprises a protein which is a function-preserving dextransucrase variant of the amino acid sequence set forth in SEQ ID NO:1, said protein having at least 98% amino acid sequence identity with the amino acid sequence set forth in SEQ ID NO: 1, wherein the amino acid sequence of the protein comprises:
   (a) a glycoside hydrolase family 70 (GH70) DED catalytic triad,
   (b) a glycoside hydrolase family 70 conserved catalytic core protein motif I corresponding to amino acids 936-942 of SEQ ID NO:1,
   (c) a glycoside hydrolase family 70 conserved catalytic core protein motif II corresponding to amino acids 458-468 of SEQ ID NO:1,
   (d) a glycoside hydrolase family 70 conserved catalytic core protein motif III corresponding to amino acids 495-505 of SEQ ID NO:1, and
   (e) a glycoside hydrolase family 70 conserved catalytic core protein motif IV corresponding to amino acids 568-582 of SEQ ID NO:1.

2. The process of claim 1, wherein the step of reacting is carried out at a temperature of between 20° C. and 40° C.

3. The process of claim 1, wherein the sucrose is present at a concentration that is between approximately 50 and 200 g.l$^{-1}$.

4. The process of claim 1, wherein pH during the step of reacting is between approximately 5 and 6.5.

5. The process of claim 1 wherein the dextransucrase is a dextransucrase comprising the amino acid sequence set forth in SEQ ID NO: 1.

6. The process of claim 1 wherein wherein α-1,6glucosidic bonds in the dextrans comprise between 97% and 98% of glucosidic bonds.

* * * * *

UNITED STATES PATENT AND TRADEMARK OFFICE
CERTIFICATE OF CORRECTION

PATENT NO. : 10,308,724 B2  
APPLICATION NO. : 15/319736  
DATED : June 4, 2019  
INVENTOR(S) : Marlène Vuillemin et al.

Page 1 of 1

It is certified that error appears in the above-identified patent and that said Letters Patent is hereby corrected as shown below:

In the Claims

Column 27, Claim 1, Line 10:
"average molar mass $M_w$, at least equal to $0.7 \times 10^9$ g.mol$^{-1}$"
Should read:
-- average molar mass $M_w$ at least equal to $0.7 \times 10^9$ g.mol$^{-1}$ --.

Column 28, Claim 6, Line 25:
"The process of claim 1 wherein wherein α-1, 6-gluco"
Should read:
-- The process of claim 1 wherein α-1, 6-gluco --.

Signed and Sealed this  
Seventh Day of April, 2020

Andrei Iancu  
*Director of the United States Patent and Trademark Office*